United States Patent
Liu et al.

(12) 
(10) Patent No.: US 11,572,563 B2
(45) Date of Patent: Feb. 7, 2023

(54) APTAMER BASED AFFINITY CAPTURE METHODS FOR THE SELECTIVE ENRICHMENT OF HUMAN IMMUNOGLOBULIN FC DOMAINS

(71) Applicant: Waters Technologies Corporation, Milford, MA (US)

(72) Inventors: Xiaoxiao Liu, Natick, MA (US); Matthew A. Lauber, North Smithfield, RI (US)

(73) Assignee: Waters Technologies Corporation, Milford, MA (US)

( * ) Notice: Subject to any disclaimer, the term of this patent is extended or adjusted under 35 U.S.C. 154(b) by 321 days.

(21) Appl. No.: 16/913,805

(22) Filed: Jun. 26, 2020

(65) Prior Publication Data

US 2020/0407723 A1    Dec. 31, 2020

Related U.S. Application Data

(60) Provisional application No. 62/866,830, filed on Jun. 26, 2019.

(51) Int. Cl.
| | |
|---|---|
| *C12N 15/115* | (2010.01) |
| *C07K 16/28* | (2006.01) |
| *G01N 33/561* | (2006.01) |
| *G01N 33/68* | (2006.01) |

(52) U.S. Cl.
CPC .......... *C12N 15/115* (2013.01); *C07K 16/283* (2013.01); *G01N 33/561* (2013.01); *G01N 33/6848* (2013.01); *G01N 2560/00* (2013.01)

(58) Field of Classification Search
CPC .................................................. C12N 15/115
USPC ............................................................. 506/9
See application file for complete search history.

(56) References Cited

U.S. PATENT DOCUMENTS 8,637,656 B2    1/2014    Nakamura et al.

FOREIGN PATENT DOCUMENTS

WO         2018019538 A1    2/2018

OTHER PUBLICATIONS

Invitation to Pay Addition Fees and, Where Applicable, Protest Fee issued in International Application No. PCT/IB2020/056089 dated Sep. 30, 2020.

*Primary Examiner* — Sean E Aeder
(74) *Attorney, Agent, or Firm* — Womble Bond Dickinson (US) LLP; Deborah M. Vernon; Dennis J. Parad

(57) ABSTRACT

A method of capturing human immunoglobulin Fc domains in a biofluid sample is provided. The method includes providing an affinity capture device. The affinity capture device includes a surface having an aptamer that is at least 80% identical to SEQ ID NO 1 immobilized onto the surface of the affinity capture device. The biofluid sample is diluted with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer.

21 Claims, 15 Drawing Sheets

Specification includes a Sequence Listing.

LCUV Overlay of mAb Eluate with Different Amount of Aptamer Immobilized

| Reagent Used | | | Protein Recovery | | |
|---|---|---|---|---|---|
| Aptamer (µg) | NIST mAb (µg) | Plasma (µL) | NIST mAb (µg) | Plasma Protein (µg) | Purity of NIST mAb (%) |
| 5 | 50 | 20 | 33.57 | 12.66 | 72.61 |
| 12.5 | | | 46.16 | 18.05 | 71.89 |
| 25 | | | 45.29 | 26.52 | 63.07 |

A.

| 2nd Washing Buffer Used | Protein Recovery from 2nd Washing Fractions | | | Protein Recovery from Eluates | | |
|---|---|---|---|---|---|---|
| | NIST mAb (μg) | Plasma (μg) | NIST mAb Purity (%) | NIST mAb (μg) | Plasma (μg) | NIST mAb Purity (%) |
| Buffer A | 0 | 2.86 | 0 | 19.46 | 12.43 | 61.02 |
| Buffer B | 0.13 | 12.01 | 1.07 | 21.56 | 3.37 | 86.47 |
| Buffer C | 9.55 | 18.63 | 33.88 | 4.71 | 1.33 | 78.03 |
| Buffer D | 8.31 | 7.25 | 53.41 | 6.68 | 12.24 | 35.29 |
| Buffer E | 15.42 | 7.81 | 66.38 | 2.86 | 12.06 | 19.18 |
| Buffer F | 17.67 | 18.47 | 48.89 | 0.5 | 0.49 | 50.94 |

FIG. 9C

APTAMER BASED AFFINITY CAPTURE METHODS FOR THE SELECTIVE ENRICHMENT OF HUMAN IMMUNOGLOBULIN FC DOMAINS

CROSS-REFERENCE TO RELATED APPLICATIONS

This application claims priority to and benefit of U.S. provisional patent application No. 62/866,830 filed on Jun. 26, 2019 and entitled "Aptamer Based Affinity Capture Methods for the Selective Enrichment of Human Immunoglobulin Fc Domains," the entire contents of which is hereby incorporated by reference.

SEQUENCE LISTING

The instant application contains a Sequence Listing which has been submitted electronically in ASCII format and is hereby incorporated by reference herein in its entirety. Said ASCII copy, created on Jun. 24, 2020, is named W-4126-US02_(102994_1005_3) SL.txt and is 5 kilobytes in size.

FIELD OF THE TECHNOLOGY

The present disclosure relates to methods and kits for using an aptamer for the selective capture of human Fc domains found in immunoglobulins or contained within a humanized monoclonal antibody. More specifically, the present technology relates to improved selectivity and binding of aptamer ligands to more effectively capture human Fc domains found in immunoglobulins.

BACKGROUND

Over the past couple of decades, the market of immunotherapy has grown exponentially. Until 2018, over 80 antibody therapeutics have been approved by the FDA, and hundreds of candidates are undergoing clinical trials. Human monoclonal antibodies (mAb) represent one of the most popular antibody therapeutic modalities and offer significantly reduced immunogenicity risks. About 80% of the FDA approved antibody drugs are either fully human or humanized antibodies with more than 90% human sequence origin. To keep up with this rapid growth in demand for human antibody therapeutics, there is a requirement for high-throughput, selective purification of target proteins from cell culture and biofluid samples.

SUMMARY

What is needed are methods and kits for using an aptamer for the selective capture of human Fc domains found in immunoglobulins or contained within a humanized monoclonal antibody. Due to the rapid growth in demand for human antibody therapeutics, the methods of the present technology have high-throughput and selective purification of target proteins from cell culture and biofluid samples. The technology is robust and facilitates human Fc capture, enabling detailed and accurate analyses during pharmacokinetic, pharmacodynamics and biotransformation studies.

It was surprisingly found that there is a competing effect between monovalent and divalent cations in a binding buffer used to bind the aptamer to a substrate as well as the surprising finding that the binding buffer was susceptible to different cations. These surprising findings resulted in a common buffer being excluded from the present method, as described in detail below. One benefit of the technology is that a complex matrix (e.g., biofludis) can be reduced in its monovalent cation concentration and the negative impact of endogenous monovalent ions is minimized, which provides improved binding capacity of an aptamer without loss of selectivity.

In one aspect, the technology relates to a method of capturing human immunoglobulin Fc domains in a biofluid sample. The method includes providing an affinity capture device comprising a surface having an aptamer that is at least 80% identical to SEQ ID NO 1 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 1 is shown below. The method can include one or more of the embodiments described herein.

SEQ ID NO 1:
5' terminus-G G rA rG rG [i2FU] rG C [i2FU] CCGA AA rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 2 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 2 is shown below. The method can include one or more of the embodiments described herein.

SEQ ID NO 2:
5' terminus-G G rA rG rG [i2FU] rG [i2FC] [i2FU] [i2FC] [i2FC] GA A A rG rG rA rA [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 3 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 3 is shown below. The method can include one or more of the embodiments described herein.

SEQ ID NO 3:
5' terminus-G G rA rG rG [i2FU] rG [i2FC] [i2FU] [i2FC] CGA A A rG rG rA rA [i2FC] [i2FU] C C—3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 4 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 4 is shown below. The method can include one or more of the embodiments described herein.

SEQ ID NO 4:
5' terminus-G(OMe) G(OMe) rA rG rG [i2FU] rG [i2FC] [i2FU] [i2FC] [i2FC] G(OMe) A(OMe) A(OMe) A(OMe) rG rG rA rA [i2FC] [i2FU] C(OMe) C(OMe)-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe) and A(OMe) represent 2'-methoxy substituted nucleotides.

In another aspect, the technology relates to a method of capturing human immunoglobulin Fc domains in a biofluid sample. The method includes providing an affinity capture device comprising a surface having an aptamer that is at least 80% identical to SEQ ID NO 5 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 5 is shown below. The method can include one or more of the embodiments described herein.

SEQ ID NO 5:
5' terminus-G G rA rG rG [i2FU] rG C U(OMe) C C G A A A rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe) represent 2'-methoxy substituted nucleotides.

In another aspect, the technology relates to a method of capturing human immunoglobulin Fc domains in a biofluid sample. The method includes providing an affinity capture device comprising a surface having an aptamer that is at least 80% identical to SEQ ID NO 6 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 6 is shown below. The method can include one or more of the embodiments described herein.

SEQ ID NO 6:
5' terminus-G(OMe) G(OMe) rA rG rG [i2FU] rG [i2FC] U(OMe) [i2FC] [i2FC] G(OMe) A(OMe) A(OMe) A(OMe) rG rG rA rA [i2FC] [i2FU] C(OMe) C(OMe)-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe), C(OMe), G(OMe) and A(OMe) represent 2'-methoxy substituted nucleotides.

In another aspect, the technology relates to a method of capturing human immunoglobulin Fc domains in a biofluid sample. The method includes providing an affinity capture device comprising a surface having an aptamer that is at least 80% identical to SEQ ID NO 7 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 7 is shown below. The method can include one or more of the embodiments described herein.

SEQ ID NO 7:
5' terminus-G(OMe) G(OMe) rA rG rG [i2FU] rG [i2FC] [i2FU] C(OMe) [i2FC] G(OMe) A(OMe) A(OMe) A(OMe) rG rG rA rA [i2FC] [i2FU] C(OMe) C(OMe)-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe) and A(OMe) represent 2'-methoxy substituted nucleotides.

In another aspect, the technology relates to a method of capturing human immunoglobulin Fc domains in a biofluid sample. The method includes providing an affinity capture device comprising a surface having an aptamer that is at least 80% identical to SEQ ID NO 8 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 8 is shown below. The method can include one or more of the embodiments described herein.

SEQ ID NO 8:
5' terminus-G(OMe) G(OMe) rA rG rG [i2FU] rG [i2FC] [i2FU] [i2FC] C(OMe) G(OMe) A(OMe) A(OMe) A(OMe) rG rG rA rA [i2FC] [i2FU] C(OMe) C(OMe)-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe) and A(OMe) represent 2'-methoxy substituted nucleotides.

In another aspect, the technology relates to a method of capturing human immunoglobulin Fc domains in a biofluid sample. The method includes providing an affinity capture device comprising a surface having an aptamer that is at least 80% identical to SEQ ID NO 9 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 9 is shown below. The method can include one or more of the embodiments described herein.

SEQ ID NO 9:
5' terminus-G G rA rG [i2FG] [i2FU] rG C [i2FU] CCGA A A rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 10 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 10 is shown below. The method can include one or more of the embodiments described herein.

SEQ ID NO 10:
5' terminus-G G rA rG rG [i2FU] [i2FG] C [i2FU] CCGA A A rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 11 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 11 is shown below. The method can include one or more of the embodiments described herein.

SEQ ID NO 11:
5' terminus-G G rA rG rG [i2FU] rG rC [i2FU] CCGA A A rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 12 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 12 is shown below. The method can include one or more of the embodiments described herein.

SEQ ID NO 12:
5' terminus-G G rA rG rG [i2FU] rG C rU CCGA A A rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides In another aspect, the technology relates to a method of capturing human immunoglobulin Fc domains in a biofluid sample. The method includes providing an affinity capture device comprising a surface having an aptamer that is at least 80% identical to SEQ ID NO 13 immobilized onto the surface of the affinity capture device. The method also includes diluting the biofluid sample with a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The human immunoglobulin Fc domains in the biofluid sample are adsorbed to the aptamer with the binding buffer. SEQ ID NO 13 is shown below. The method can include one or more of the embodiments described herein.

SEQ ID NO 13:
5' terminus-G G rA rG rG [i2FU] rG C U(OMe) CCGA AA rG rG A A [i2FC] [i2FU] C C-3' terminus
where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe) represents 2'-methoxy substituted nucleotides.

In some embodiments, the aptamer is at least 85%, 90%, 95%, 98% or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). The aptamer can be, for example, 85%, 86%, 87%, 88%, 89%, 90%, 91%, 92%, 93%, 94%, 95%, 96%, 97%, 98%, or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). These percentages can be used to form a range, for example, the aptamer can be between 85% to 99% or 90% to 95% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). In some embodiments, the aptamer is a 23-nucleotide aptamer. The aptamer can be a 23-nucleotide aptamer having an extended or truncated sequence of about 3 residues. The aptamer can be a 23-nucleotide aptamer having an extended or truncated sequence of about 5 residues. The aptamer can be covalently immobilized or non-covalently immobilized onto the surface of the affinity capture device.

In some embodiments, the binding buffer has a concentration of monovalent cations less than about 50 mM. The binding buffer can have a concentration of monovalent cations less than about 30 mM. In some embodiments, the pH of the binding buffer is between about 5 and about 9. The pH of the binding buffer can be between about 6 to about 8. The pH of the binding buffer can be about 7.2. For example, the pH of the binding buffer can be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. These pH values can be used to form a range, for example, from about 7.0 to about 7.4 or from about 7.1, to about 7.3.

The biofluid sample can be diluted. For example, the biofluid sample can be diluted by a factor of 2, 10, or 20. In some embodiments, the biofluid sample is diluted by a factor of 1, 3, 4, 5, 6, 7, 8, 9, 10, 11, 12, 13, 14, 15, 16, 17, 18, 19, or 20. The dilution factors can be used to form a range, for example, from about 2 to about 20 or from about 2 to about 10, or from about 10 to about 20. In some embodiments, the biofluid sample is diluted to obtain a total monovalent cation concentation of the biofluid sample of no greater than 100 mM, no greater than 50 mM or no greater than 30 mM. The total monovalent cation concentration of the diluted biofluid sample can be no greater than 100 mM, 90 mM, 80 mM, 70 mM, 60 mM, 50 mM, 40 mM, 30 mM, 20 mM, or 10 mM.

In some embodiments, the method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. In some embodiments, the ammonium concentration is between about 50 mM to about 500 mM. The eluent can have a pH between about 6.5 to about 8.0. The eluent can have a pH of about 6.5, 6.6, 6.7, 6.8, 6.9, 7.0, 7.1, 7.2, 7.3, 7.4, 7.5, 7.6, 7.7, 7.8, 7.9, or 8.0. These pH values can be used to form a range, for example, from between about 7.0 to about 8.0 or from about 6.5 to about 7.5.

In some embodiments, the method also includes washing the adsorbed human immunoglobulin Fc domains with the binding buffer. The method can also include washing the adsorbed human immunoglobulin Fc domains with a buffer comprising Cat In some embodiments, the concentration of the magnesium cation is between about 50 µM to about 1 mM. The concentration of the magnesium cation can be, for example, 50 µM, 100 µM, 150 µM, 200 µM, 250 µM, 300 µM, 350 µM, 400 µM, 450 µM, 500 µM, 550 µM, 600 µM, 650 µM, 700 µM, 750 µM, 800 µM, 850 µM, 900 µM, 950 µM, or 1000 µM. These concentrations can be used to form a range, for example, between about 50 µM to about 500 µM or from about 50 µM to about 200 µM.

In some embodiments, the method also includes analyzing the eluted human immunoglobulin Fc domain with a detector. The detector can be a sandwiched enzyme linked immunosorbent assay or a mass spectrometer.

In some embodiments, the human immunoglobulin Fc domains are contained within a humanized monoclonal antibody. The method can also include purifying the humanized monoclonal antibody.

In another aspect, the technology relates to a method of eluting a human immunoglobulin Fc domain from an immobilized aptamer. The method includes providing an affinity capture device having a surface having an aptamer that is at least 80% identical to SEQ ID NO 1 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 2 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 3 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 4 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 5 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 6 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 7 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 8 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 9 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 10 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 11 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 12 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In another aspect, the technology relates to a method of eluting a human immunoglobulin Fc domain from an immobilized aptamer. The method includes providing an affinity capture device having a surface having an aptamer that is at least 80% identical to SEQ ID NO 13 immobilized onto the surface of the affinity capture device. The immobilized aptamer has an adsorbed human immunoglobulin Fc domain. The method also includes eluting the adsorbed human immunoglobulin Fc domain from the immobilized aptamer using an eluent having an ammonium concentration between about 10 mM to about 1000 mM. The ammonium is in the form of tetramethylammonium, triethylammonium, ammonium formate, or ammonium acetate. The method can include one or more of the embodiments described herein.

In some embodiments, the aptamer is at least 85%, 90%, 95%, 98% or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). The aptamer can be, for example, 85%, 86%, 87%, 88%, 89%, 90%, 91%, 92%, 93%, 94%, 95%, 96%, 97%, 98%, or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). These percentages can be used to form a range, for example, the aptamer can be between 85% to 99% or 90% to 95% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). In some embodiments, the aptamer is a 23-nucleotide aptamer. The aptamer can be a 23-nucleotide aptamer having an extended or truncated sequence of about 3 residues. The aptamer can be a 23-nucleotide aptamer having an extended or truncated sequence of about 5 residues. The aptamer can be covalently immobilized or non-covalently immobilized onto the surface of the affinity capture device.

In some embodiments, the ammonium concentration is between about 50 mM to about 500 mM. For example, the ammonium concentration can be about 50 mM, 100 mM, 150 mM, 200 mM, 250 mM, 300 mM, 350 mM, 400 mM, 450 mM, or 500 mM. These values can be used to form a range, for example, from between about 200 mM to about 400 mM.

In some embodiments, the eluent has a pH between about 6.5 to about 8.0. For example, the eluent can have a pH of about 6.5, 6.6, 6.7, 6.8, 6.9, 7.0, 7.1, 7.2, 7.3, 7.4, 7.5, 7.6, 7.7, 7.8, 7.9, or 8.0. These pH values can be used to form a range, for example, between about 7.0 to 8.0 or between about 6.5 to about 7.0.

The method can also include analyzing the eluted human immunoglobulin Fc domain with a detector. The detector can be a sandwiched enzyme linked immunosorbent assay or a mass spectrometer.

In some embodiments, the human immunoglobulin Fc domains are contained within a humanized monoclonal antibody. The method can also include purifying the humanized monoclonal antibody.

In another aspect, the technology features a kit. The kits includes an affinity capture device having a surface having an aptamer that is at least 80% identical to SEQ ID NO 1 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 2 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 3 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 4 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 5 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 6 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 μM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 7 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 8 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 9 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 10 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 11 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 12 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In another aspect, the technology features a kit. The kits includes an affinity capture device having a surface having an aptamer that is at least 80% identical to SEQ ID NO 13 immobilized onto the surface of the affinity capture device. The kit also includes a vial of a binding buffer. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include one or more of the embodiments described herein.

In some embodiments, the aptamer is at least 85%, 90%, 95%, 98% or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). The aptamer can be, for example, 85%, 86%, 87%, 88%, 89%, 90%, 91%, 92%, 93%, 94%, 95%, 96%, 97%, 98%, or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). These percentages can be used to form a range, for example, the aptamer can be between 85% to 99% or 90% to 95% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). In some embodiments, the aptamer is a 23-nucleotide aptamer. The aptamer can be a 23-nucleotide aptamer having an extended or truncated sequence of about 3 residues. The aptamer can be a 23-nucleotide aptamer having an extended or truncated sequence of about 5 residues. The aptamer can be covalently immobilized or non-covalently immobilized onto the surface of the affinity capture device.

In some embodiments, the binding buffer has a concentration of monovalent cations less than about 50 mM. The binding buffer can have a concentration of monovalent cations less than about 30 mM. In some embodiments, the pH of the binding buffer is between about 5 and about 9. The pH of the binding buffer can be between about 6 to about 8. The pH of the binding buffer can be about 7.2. For example, the pH of the binding buffer can be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. These pH values can be used to form a range, for example, from about 7.0 to about 7.4 or from about 7.1, to about 7.3.

In some embodiments, the concentration of the magnesium cation is between about 50 µM to about 1 mM. The concentration of the magnesium cation can be, for example, 50 µM, 100 µM, 150 µM, 200 µM, 250 µM, 300 µM, 350 µM, 400 µM, 450 µM, 500 µM, 550 µM, 600 µM, 650 µM, 700 µM, 750 µM, 800 µM, 850 µM, 900 µM, 950 µM, or 1000 µM. These concentrations can be used to form a range, for example, between about 50 µM to about 500 µM or from about 50 µM to about 200 µM.

In some embodiments, the kit also includes a vial of an eluent having an ammonium concentration between about 10 mM to about 1000 mM. The ammonium can be in the form of tetramethylammonium, triethylammonium, ammonium formate, or ammonium acetate.

In some embodiments, the kit also includes a vial of a buffer comprising $Ca^+$. The buffer can be concentrated and the kit can also include instructions for diluting the concentrated buffer to a working concentration using water. For example, the working concentration of the buffer can be between about 0.5 and 20 mM and the concentrated concentration can be between about 20 to 500 mM.

In some embodiments, the vial of buffer comprises 10 mM Tris, 5 mM $CaCl_2$) at a pH of 7.2.

In some embodiments, the kit also includes instructions for performing any one of the methods described herein.

In another aspect, the technology relates to a kit. The kit includes an affinity capture device including a surface having an aptamer that is at least 80% identical to SEQ ID NO 1 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 2 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 3 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 4 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 5 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 6 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 7 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 8 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 9 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 10 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 11 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 12 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In another aspect, the technology relates to a kit. The kit includes an affinity capture device including a surface having an aptamer that is at least 80% identical to SEQ ID NO 13 immobilized onto the surface of the affinity capture device. The kit also includes a vial of an eluent having an ammonium concentration between about 10 mM to about 1000 mM, wherein the ammonium is in the form of tetramethylammonium, triethylammonium, ammonium formate, or ammonium acetate. The kit can include one or more the embodiments described herein.

In some embodiments, the aptamer is at least 85%, 90%, 95%, 98% or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). The aptamer can be, for example, 85%, 86%, 87%, 88%, 89%, 90%, 91%, 92%, 93%, 94%, 95%, 96%, 97%, 98%, or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). These percentages can be used to form a range, for example, the aptamer can be between 85% to 99% or 90% to 95% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). In some embodiments, the aptamer is a 23-nucleotide aptamer. The aptamer can be a 23-nucleotide aptamer having an extended or truncated sequence of about 3 residues. The aptamer can be a 23-nucleotide aptamer having an extended or truncated sequence of about 5 residues. The aptamer can be covalently immobilized or non-covalently immobilized onto the surface of the affinity capture device.

In some embodiments, the ammonium concentration is between about 50 mM to about 500 mM. For example, the ammonium concentration can be about 50 mM, 100 mM, 150 mM, 200 mM, 250 mM, 300 mM, 350 mM, 400 mM, 450 mM, or 500 mM. These values can be used to form a range, for example, from between about 200 mM to about 400 mM.

In some embodiments, the eluent has a pH between about 6.5 to about 8.0. For example, the eluent can have a pH of about 6.5, 6.6, 6.7, 6.8, 6.9, 7.0, 7.1, 7.2, 7.3, 7.4, 7.5, 7.6, 7.7, 7.8, 7.9, or 8.0. These pH values can be used to form a range, for example, between about 7.0 to 8.0 or between about 6.5 to about 7.0.

The kit can also include instructions for performing any one of the methods described herein.

BRIEF DESCRIPTION OF THE FIGURES

FIG. 2A depicts an example of the impact of divalent cations in binding buffer. Recovery and breakthrough for 5 µg of aptamer immobilized onto 40 µL of streptavidin resin when loaded with 100 µg of human IgG. Buffer A contains: 10 mM Tris HCl, pH 7.2; Buffer B contains: 10 mM Tris HCl, 5 mM $MgCl_2$, pH 7.2; Buffer C contains: 10 mM Tris HCl, 5 mM $CaCl_2$); Buffer D contains: 10 mM Tris HCl, 5 mM $MnCl_2$; Buffer E contains: 10 mM Tris HCl, 5 mM Zn acetate. Buffer Nakamura et al. contains: 145 mM NaCl, 5.4 mM KCl, 1.8 mM $CaCl_2$), 0.8 mM $MgCl_2$, 20 mM Tris HCl, pH 7.6. Experimental details can be found in Example 1.

FIG. 2B depicts an example of the impact of divalent cations in binding buffer. Recovery and breakthrough for 5 µg of aptamer immobilized onto 40 µL of streptavidin resin when loaded with 100 µg of human IgG. Buffer A contains: 10 mM Tris HCl, pH 7.2; Buffer B contains: 10 mM Tris HCl, 5 mM $MgCl_2$, pH 7.2; Buffer C contains: 10 mM Tris HCl, 5 mM $CaCl_2$); Buffer D contains: 10 mM Tris HCl, 5 mM $MnCl_2$; Buffer E contains: 10 mM Tris HCl, 5 mM Zn acetate. Buffer Nakamura et al contains: 145 mM NaCl, 5.4 mM KCl, 1.8 mM $CaCl_2$), 0.8 mM $MgCl_2$, 20 mM Tris $HCl_2$, pH 7.6. Experimental details can be found in Example 1.

FIG. 3A depicts an example of the impact of monovalent cations in binding buffer. Recovery and breakthrough for 5 µg of aptamer immobilized onto 40 µL of streptavidin resin when loaded with 100 µg of human IgG. Buffer A contains: 10 mM Tris HCl, 150 mM NaCl, pH 7.2; Buffer B contains: 10 mM Tris HCl, 150 mM NaCl, 5 mM KCl. pH 7.2; Buffer C contains: 10 mM Tris HCl, 150 mM NaCl, 5 mM $MgCl_2$ pH 7.2; Buffer D contains: 10 mM Tris HCl, 150 mM NaCl, 5 mM $CaCl_2$, pH 7.2; Buffer E contains: 10 mM Tris HCl, 150 mM NaCl, 5 mM $MnCl_2$, pH 7.2; Buffer F contains: 10 mM Tris HCl, 150 mM NaCl, 5 mM Zn acetate pH 7.2. Buffer G contains: 10 mM Tris HCl, 5 mM $MgCl_2$, pH 7.2; Buffer H contains: 10 mM Tris HCl, 5 mM $CaCl_2$, pH 7.2; Buffer 1 contains: 10 mM Tris HCl, 5 mM $MnCl_2$, pH 7.2; Buffer J contains: 10 mM Tris HCl, 5 mM Zn acetate, pH 7.2. Experimental details can be found in Example 1.

FIG. 3B depicts an example of the impact of monovalent cations in binding buffer. Recovery and breakthrough for 5 µg of aptamer immobilized onto 40 µL of streptavidin resin when loaded with 100 µg of human IgG. Buffer A contains: 10 mM Tris HCl, 150 mM NaCl, pH 7.2; Buffer B contains: 10 mM Tris HCl, 150 mM NaCl, 5 mM KCl, pH 7.2; Buffer C contains: 10 mM Tris HCl, 150 mM NaCl, 5 mM $MgCl_2$, pH 7.2; Buffer D contains: 10 mM Tris HCl, 150 mM NaCl, 5 mM $CaCl_2$), pH 7.2; Buffer E contains: 10 mM Tris HCl, 150 mM NaCl, 5 mM $MnCl_2$, pH 7.2; Buffer F contains: 10 mM Tris HCl, 150 mM NaCl, 5 mM Zn acetate, pH 7.2. Buffer G contains: 10 mM Tris HCl, 5 mM $MgCl_2$, pH 7.2; Buffer H contains: 10 mM Tris HCl, 5 mM $CaCl_2$), pH 7.2; Buffer I contains: 10 mM Tris HCl, 5 mM $MnCl_2$, pH 7.2; Buffer J contains: 10 mM Tris HCl, 5 mM Zn acetate, pH 7.2. Experimental details can be found in Example 1.

FIG. 4A depicts an example of the impact of pH buffer component: tris vs. phosphate. Recovery and breakthrough for 5 µg of aptamer immobilized onto 40 µL of streptavidin resin when loaded with 100 µg of human IgG. Buffer A contains: 20 mM Sodium Phosphate, pH 7.0; Buffer B contains: 20 mM Sodium Phosphate, 150 mM NaCl, pH 7.0; Buffer C contains: 20 mM Sodium Phosphate, 5 mM $MgCl_2$ pH 7.0; Buffer D contains: 10 mM Tris HCl pH 7.2; Buffer E contains: 10 mM Tris HCl, 150 mM NaCl, pH 7.2; Buffer F contains: 10 mM Tris HCl, 5 mM $MgCl_2$ pH 7.2. Experimental details can be found in Example 1.

FIG. 4B depicts an example of the impact of pH buffer component: tris vs. phosphate. Recovery and breakthrough for 5 µg of aptamer immobilized onto 40 µL of streptavidin resin when loaded with 100 µg of human IgG. Buffer A contains: 20 mM Sodium Phosphate, pH 7.0; Buffer B contains: 20 mM Sodium Phosphate, 150 mM NaCl, pH 7.0; Buffer C contains: 20 mM Sodium Phosphate, 5 mM $MgCl_2$, pH 7.0; Buffer D contains: 10 mM Tris HCl, pH 7.2; Buffer E contains: 10 mM Tris HCl, 150 mM NaCl, pH 7.2; Buffer F contains: 10 mM Tris HCl, 5 mM $MgCl_2$, pH 7.2. Experimental details can be found in Example 1.

FIG. 5 depicts an example of a non-specific binding study with different binding buffer. Recovery and breakthrough for 5 µg of aptamer immobilized onto 40 µL of streptavidin resin when loaded with 100 µg of human IgG. Buffer A contains: 10 mM Tris HCl, 150 mM NaCl, 5 mM $MgCl_2$, pH 7.2; Buffer B contains: 10 mM Tris HCl, 150 mM NaCl, 5 mM $CaCl_2$, pH 7.2; Buffer C contains: 10 mM Tris HCl, 150 mM NaCl, 5 mM $MnCl_2$, pH 7.2; Buffer D contains: 10 mM Tris HCl, 150 mM NaCl, 5 mM Zn acetate, pH 7.2. Buffer E contains: 10 mM Tris HCl, 5 mM $MgCl_2$, pH 7.2; Buffer F contains: 10 mM Tris HCl, 5 mM $CaCl_2$), pH 7.2; Buffer G contains: 10 mM Tris HCl, 5 mM $CaCl_2$), pH 7.2; Buffer H contains: 10 mM Tris HCl, 5 mM Zn acetate, pH 7.2. Experimental details can be found in Example 2.

FIG. 6 depicts an example of the impact of Mg concentration in binding buffer and selection of elution buffer. Recovery and breakthrough for 5 µg of aptamer immobilized onto 40 µL of streptavidin resin when loaded with 100 µg of human IgG. Binding Buffer contains 10 mM Tris HCl, pH 7.2 with $MgCl_2$, concentration range from 1 µM to 200 mM. Captured hIgG was eluted with either 200 mM $NH_4$ Acetate or 200 mM EDTA. Experimental details can be found in Example 2.

FIG. 7 is an example of the binding capacity of aptamer versus single domain antibody $V_{HH}$. Recovery and breakthrough for 40 µL of streptavidin resin with vary amount of anti-human Fc ligand (aptamer or $V_{HH}$) immobilized when loaded with 500 µg of human IgG. Experimental details can be found in Example 3.

FIG. 8A is an LC-UV profile of plasma sample, according to an illustrative embodiment of the technology.

FIG. 8B is an LC-UV profile of aptamer flow through, according to an illustrative embodiment of the technology.

FIG. 8C is an LC-UV profile of eluate fractions, according to an illustrative embodiment of the technology.

FIG. 8D is an LCUV overlay of eluate fractions recovered from 40 µg of streptavidin resin with 5 µg, 12.5 µg and 25 µg aptamer immobilized, according to an illustrative embodiment of the technology.

FIG. 8E is a table showing the loading and recovery of NIST mAb and plasma protein that were calculated, according to an illustrative embodiment of the technology.

FIG. 9A, FIG. 9B, and FIG. 9C are examples of a procedure to reduce non-specific binding of aptamer against endogenous protein from rat plasma. Eluate and washing fractions for 5 µg of aptamer immobilized onto 40 µL of streptavidin resin when loaded with 25 µg of NIST mAb and 20 µL of rat plasma.

FIG. 9A is an overlay of LC-UV profile of aptamer $2^{nd}$ washing fractions with washing buffer A through F, according to an illustrative embodiment of the technology. FIG. 9A is an example of an overlay of LC-UV profile of aptamer $2^{nd}$ washing fractions with washing buffer A through F (top to bottom). Buffer A contains: 10 mM Tris HCl, 0.5 mM $MgCl_2$, pH 7.2 (Binding buffer); Buffer B contains: 10 mM Tris HCl, 5 mM $CaCl_2$, pH 7.2; Buffer C contains: 145 mM NaCl, 5.4 mM KCl, 1.8 mM $CaCl_2$, 0.8 mM $MgCl_2$, 20 mM Tris HCl, pH 7.6 (Nakamura et. al.); Buffer D contains: 20 mM phosphate, pH 7.0; Buffer E contains: 0.1 M glycine HCl pH 2.7; Buffer F contains: 150 mM NaCl.

FIG. 9B is an overlay of LC-UV profile of aptamer eluate fractions after $2^{nd}$ washing step with washing buffer A through F, according to an illustrative embodiment of the technology. FIG. 9B is an example of an overlay of LC-UV profile of aptamer eluate fractions after $2^{nd}$ washing step with washing buffer A through F (top to bottom). Experimental details can be found in Example 4.

FIG. 9C is a chart showing the calculated recovery of NIST mAb and plasma protein in both $2^{nd}$ washing and eluate fractions with $2^{nd}$ washing buffer A through F, according to an illustrative embodiment of the technology. FIG. 9C is an example of a procedure to reduce non-specific binding of aptamer against endogenous protein from rat plasma. Eluate and washing fractions for 5 µg of aptamer immobilized onto 40 µL of streptavidin resin when loaded with 25 µg of NIST mAb and 20 µL of rat plasma. C. The calculated recovery of NIST mAb and plasma protein in both $2^{nd}$ washing and eluate fractions with $2^{nd}$ washing buffer A through F (top to bottom). Buffer A contains: 10 mM Tris HCl, 0.5 mM $MgCl_2$, pH 7.2 (Binding buffer); Buffer B contains: 10 mM Tris HCl, 5 mM $CaCl_2$, pH 7.2; Buffer C contains: 145 mM NaCl, 5.4 mM KCl, 1.8 mM $CaCl_2$, 0.8 mM $MgCl_2$, 20 mM Tris HCl, pH 7.6 (Nakamura et. al.); Buffer D contains: 20 mM phosphate, pH 7.0; Buffer E contains: 0.1 M glycine HCl, pH 2.7; Buffer F contains: 150 mM NaCl. Experimental details can be found in Example 4.

DETAILED DESCRIPTION

Figure 1:
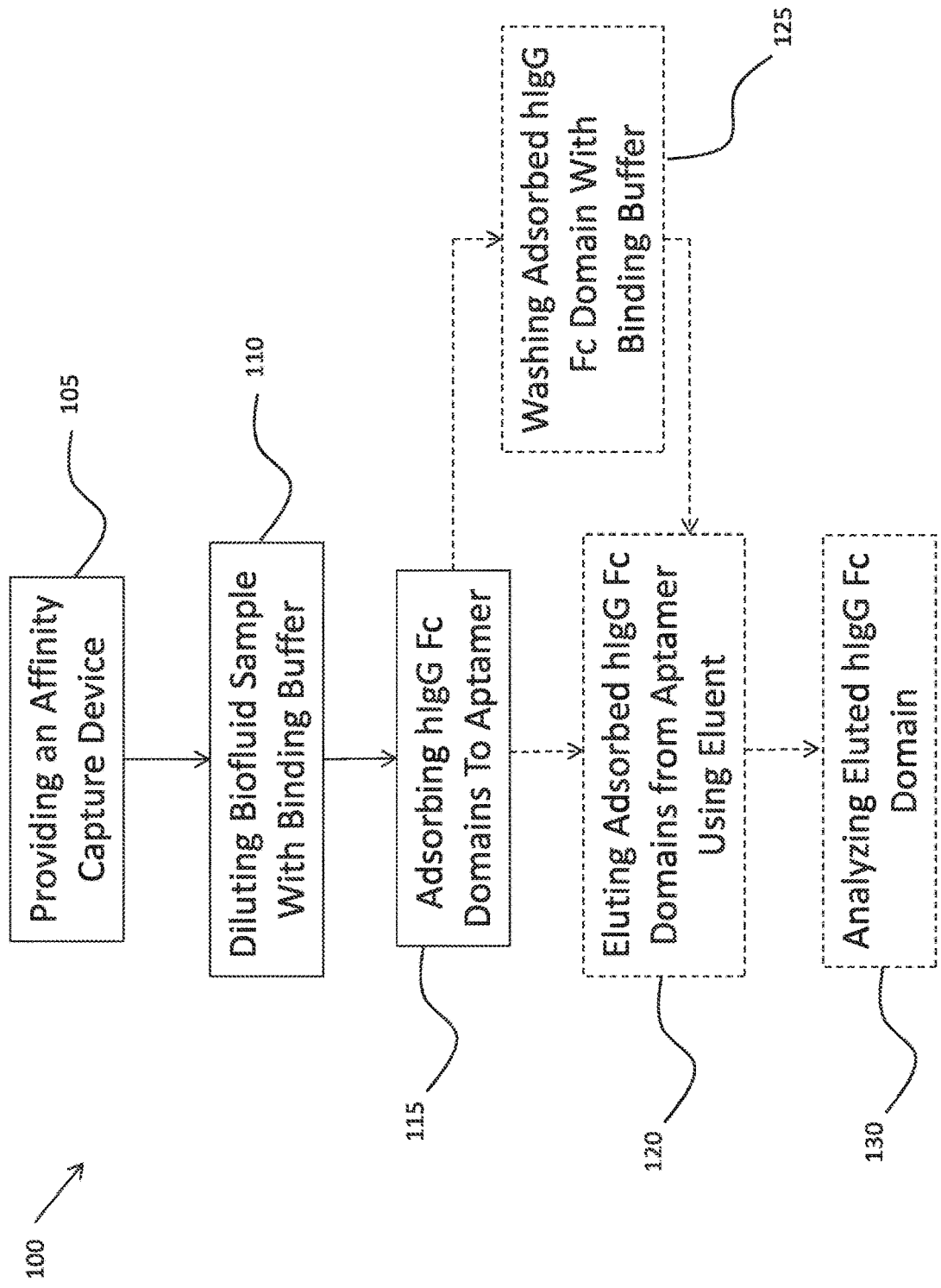
FIG. 1 is a flow chart of a method of capturing human immunoglobulin Fc domains in a biofluid sample, according to an illustrative embodiment of the technology.

The technology includes methods and kits for using an aptamer for the selective capture of human Fc domains found in immunoglobulins. With this technology, the selectivity and binding capacity of certain aptamer ligands have been significantly improved, making it more effective it is applicability to the capture of human IgG (hIgG). Together with particular embodiments of aptamer immobilized resins and form factors for affinity capture devices, a powerful and robust technology for anti-human Fc capture has been devised. In one exemplary embodiment, and an optimized workflow, an immobilized aptamer resin is contained within a pipet tip and used for the rapid and selective capture of the humanized Fc domain contained within a monoclonal antibody (mAb) therapeutic from a sample of biofluid obtained during preclinical rodent or monkey trials.

Affinity capture approaches are some of the most powerful techniques for facilitating antibody purification, antibody characterization, and the development of clinical diagnostics. The enrichment of target antibodies can be simplified to a one-step process if appropriately designed affinity consumables are available. Aptamers, a group of short, single-stranded oligonucleotides with unique 3D conformation have been proposed as novel affinity ligands for high capacity and high selectivity enrichment. These chemically synthesized molecules are usually less than 10 kDa in size and their high affinity capability can be achieved by targeted screening via SELEX (Systematic Evolution of Ligands by Exponential Enrichment) amplification. Because of their comparatively small size, aptamers can achieve high surface coverage on solid supports through controllable immobilization, minimize any possible steric hindrance, and ensure the high yield of target protein with significantly reduced sample preparation time. Besides, being that they are in vitro synthesized oligonucleotides, aptamers are often highly stable and they can be manufactured efficiently and economically, with potentially better batch-to-batch reproducibility versus protein-based ligands.

Anti-human Fc aptamer ligands comprised of 40 or fewer nucleotides are shown in U.S. Pat. No. 8,637,656 to Nakamura et al. (incorporated by reference herein in its entirety) as protein A alternatives for the purification of antibody and biotherapeutics. Previous studies involving these aptamers have shown that a GGUGCU bulging motif is essential for the selective interaction with human IgG Fc domain Two stem structures at both ends of the bulge motif, together with a 3 or 4 nucleotide loop form the critical affinity motif of the molecule. Incorporation of 2'-fluoro groups within select pyrimidine nucleotide residues was also applied to improve the stability and selectivity of the aptamer. In a crystallography investigation of the human IgG-aptamer complex it was found that this optimized aptamer interacts with several conserved residues of the human IgG Fc domain mainly via van der Waals contacts and hydrogen bonds rather than electrostatic forces. Moreover, it was suggested that the binding structure of the aptamer can be stabilized by calcium ions and that binding can be reversed through calcium chelation. However, despite these valuable fundamental studies of an anti-human Fc aptamer, there remains a need for robust methods that facilitate human Fc capture so that more detailed and more accurate analyses can be performed during pharmacokinetic, pharmacodynamic and biotransformation studies.

With this technology, a novel, aptamer-based sample preparation method is provided for the selective capture of human immunoglobulin Fc domains. A 23-nucleotide aptamer with the any one of SEQ ID NO 1-13 can be employed. In addition, other sequences described in U.S. Pat. No. 8,637,656 can be used and are incorporated herein by reference in their entirety. Namely, SEQ ID NOs 2-13 have been shown to have a capacity for the selective capture of human immunoglobulin and are equivalent in their applicability to SEQ ID NO 1 with respect to the instant technology. Some of the sequences described in U.S. Pat. No. 8,637,656 may lack the species selectivity necessary to achieve selective capture of human Fc domains from animal, pre-clinical biofluids. These aptamer sequences might mimic the comparatively broad specificity of protein A. Nevertheless, it is believed they too will be amenable to the methods of the instant invention, potentially for an alternative means for the purification of monoclonal antibodies from cell culture media. Each of SEQ ID Nos 1-13 are shown below.

SEQ ID NO 1:
5' terminus-G G rA rG rG [i2FU] rG C [i2FU] C C G A A A rG rG A A [i2FC] [i2FU] C C-3' terminus SEQ ID NO 2:
5' terminus-G G rA rG rG [i2FU] rG [i2FC] [i2FU] [i2FC] [i2FC] GA A A rG rG rA rA [i2FC] [i2FU] C C-3' terminus SEQ ID NO 3:
5' terminus-G G rA rG rG [i2FU] rG [i2FC] [i2FU] [i2FC] C G A A A rG rG rA rA [i2FC] [i2FU] C C—3' terminus SEQ ID NO 4:
5' terminus-G(OMe) G(OMe) rA rG rG [i2FU] rG [i2FC] [i2FU] [i2FC] [i2FC] G(OMe) A(OMe) A(OMe) A(OMe) rG rG rA rA [i2FC] [i2FU] C(OMe) C(OMe)-3' terminus SEQ ID NO 5:
5' terminus-G G rA rG rG [i2FU] rG C U(OMe) C C G A A A rG rG A A [i2FC] [i2FU] C C-3' terminus SEQ ID NO 6:
5' terminus-G(OMe) G(OMe) rA rG rG [i2FU] rG [i2FC] U(OMe) [i2FC] [i2FC] G(OMe) A(OMe) A(OMe) A(OMe) rG rG rA rA [i2FC] [i2FU] C(OMe) C(OMe)-3' terminus SEQ ID NO 7:
5' terminus-G(OMe) G(OMe) rA rG rG [i2FU] rG [i2FC] [i2FU] C(OMe) [i2FC] G(OMe) A(OMe) A(OMe) A(OMe) rG rG rA rA [i2FC] [i2FU] C(OMe) C(OMe)-3' terminus SEQ ID NO 8:
5' terminus-G(OMe) G(OMe) rA rG rG [i2FU] rG [i2FC] [i2FU] [i2FC] C(OMe) G(OMe) A(OMe) A(OMe) A(OMe) rG rG rA rA [i2FC] [i2FU] C(OMe) C(OMe)-3' terminus SEQ ID NO 9:
5' terminus-G G rA rG [i2FG] [i2FU] rG C [i2FU] CCGA AA rG rG A A [i2FC] [i2FU] C C-3' terminus SEQ ID NO 10:
5' terminus-G G rA rG rG [i2FU] [i2FG] C [i2FU] CCGA A rG rG A A [i2FC] [i2FU] C C-3' terminus SEQ ID NO 11:
5' terminus-G G rA rG rG [i2FU] rG rC [i2FU] CCGA A A rG rG A A [i2FC] [i2FU] C C-3' terminus SEQ ID NO 12:
5' terminus-G G rA rG rG [i2FU] rG C rU CCGA A A rG rG A A [i2FC] [i2FU] C C-3' terminus SEQ ID NO 13:
5' terminus-G G rA rG rG [i2FU] rG C U(OMe) CCGA AA rG rG A A [i2FC] [i2FU] C C-3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe), C(OMe), G(OMe) and A(OMe) represent 2'-methoxy substituted nucleotides.

In all embodiments of this technology, the aptamer ligand is immobilized to substrates suitable for performing affinity capture and sample enrichment. Substrates include, but are not limited to, the surfaces of microvolume plates, pipet tips, and labware as well as both porous and non-porous resins comprised of polymers, silica and organosilica.

When an aptamer is immobilized onto a resin, the resin can then be immobilized onto a consumable (e.g., microvolume plates, pipet tips, and/or other labware). In this way, the resin can be used to increase the surface area and/or amount of aptamer bound to the surface. In other embodiments, the resin having an immobilized aptamer can be used as a stationary phase in a chromatography column.

The sequence of aptamer can be modified from either its 5'- or 3'-terminus or one of its internal residues. This sequence modification can impart a chemical handle and an optional spacer arm moiety, including but not limited to hydrophilic molecular compositions, such as 2 to 50 repeat units of polyethylene glycol or polyethylene oxide. In addition, this sequence modification can be used for the sake of achieving oriented immobilization. For instance, with a primary amino group added to either the 5 or 3' terminus, the aptamer can be modified via a nucleophilic/electrophilic reaction scheme to yield a single-point linkage to another molecule, surface, or resin that would also impart defined directionality. In some embodiments, the above described chemical handle can include a biotin, amine, carboxyl or thiol group. Upon immobilization and storage, the immobilized aptamer can be augmented with one or more nuclease inhibitors to improve its shelf life. Nucleases can also be added in storage solutions and working buffers to extend the stability of immobilized aptamer.

FIG. 1 shows a method 100 of capturing human immunoglobulin Fc domains in a biofluid sample. The method includes providing an affinity capture device 105. The affinity capture device has a surface having an aptamer that is at least 80% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13) immobilized onto the surface of the affinity capture device. The aptamer can be 85%, 90%, 95%, 98%, or 99% identical to SEQ ID NO 1 (or SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 10, SEQ ID NO 11, SEQ ID NO 11, SEQ ID NO 12, or SEQ ID NO 13). The aptamer can be a 23 nucleotide aptamer. The aptamer can be a 23 nucleotide aptamer having an extended or truncated sequence of about 3 or about 5 residues. The aptamer can be non-covalently or covalently immobilized onto the surface of the affinity capture device.

The method 100 also includes diluting the biofluid sample with a binding buffer 110. The binding buffer includes (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The method 100 also includes adsorbing the human immunoglobulin Fc domains 115 in the biofluid sample to the aptamer with the binder buffer.

Figure 2A:
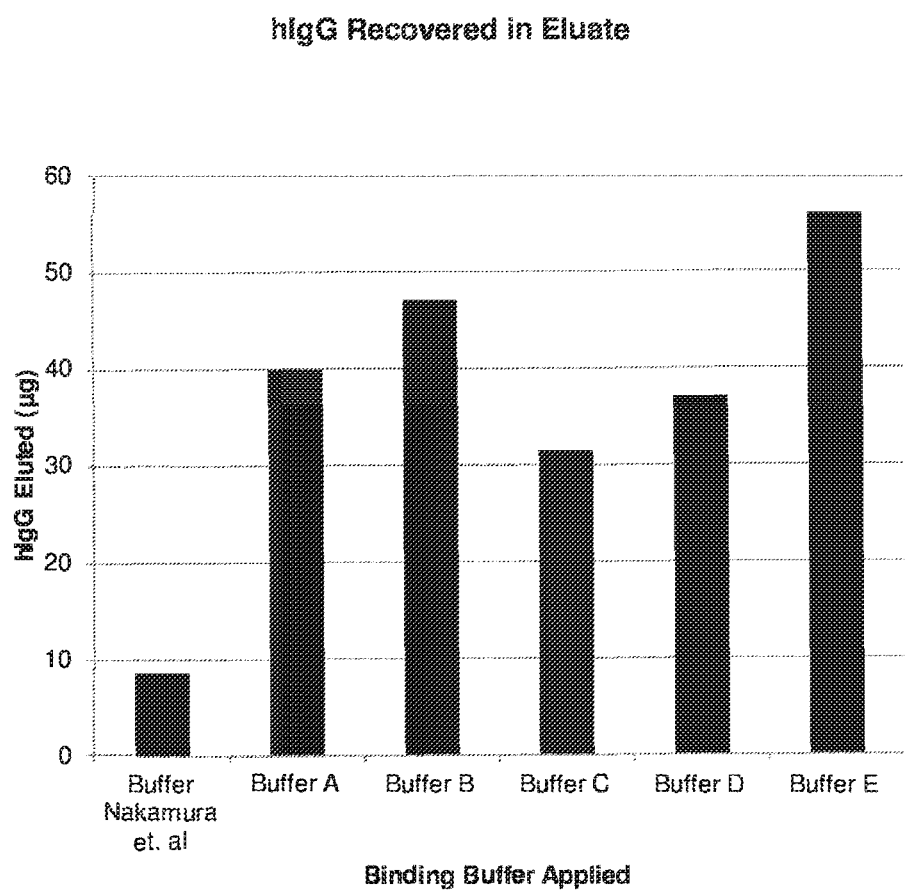
FIG. 2A is a chart showing the impact of divalent cations on hIgG recovered in eluate for various binding buffers, according to an illustrative embodiment of the technology.
Figure 4A:
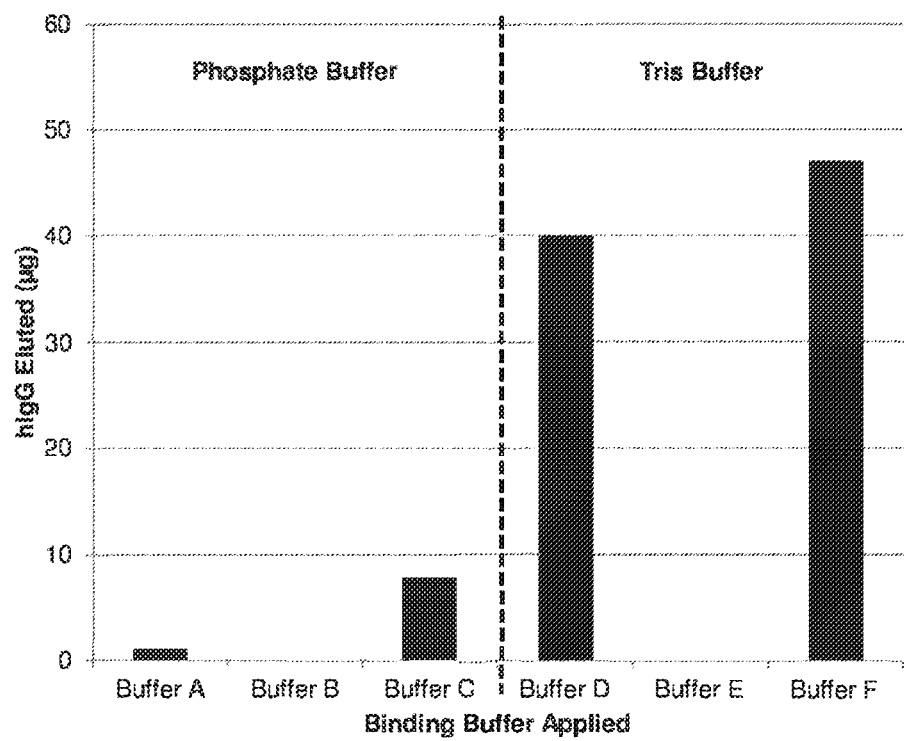
FIG. 4A is a chart showing the impact of pH buffer component (tris vs. phosphate) on hIgG recovered in eluate, according to an illustrative embodiment of the technology.
Figure 4B:
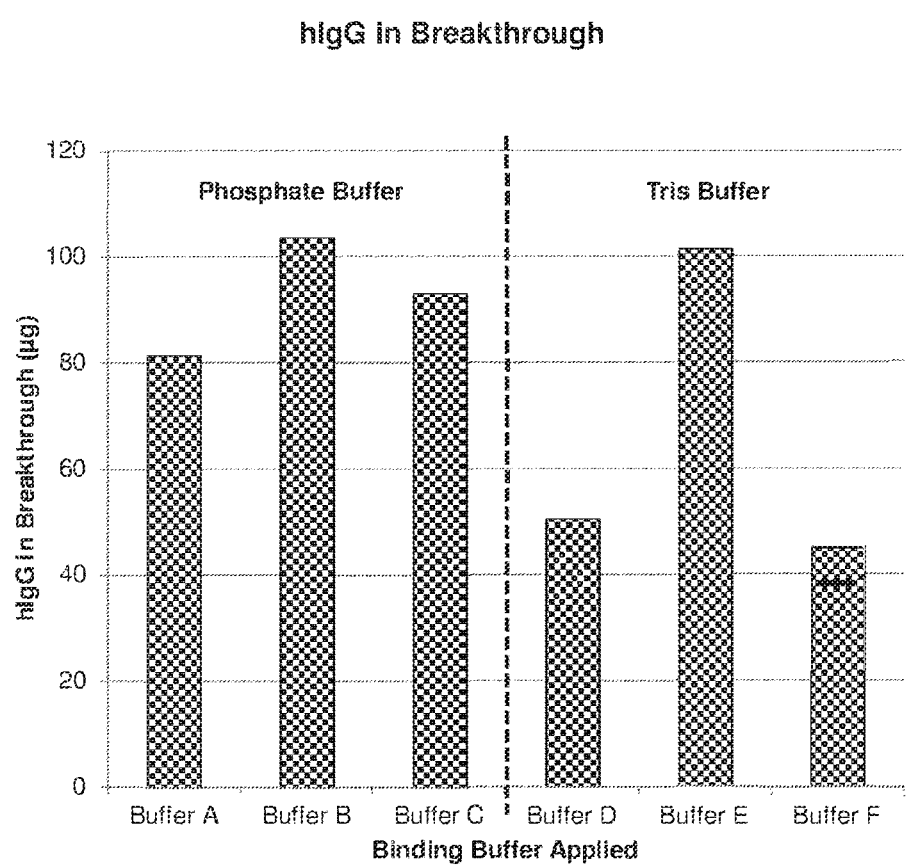
FIG. 4B is a chart showing the impact of pH buffer component (tris vs. phosphate) on hIgG in breakthrough, according to an illustrative embodiment of the technology.
Figure 5:
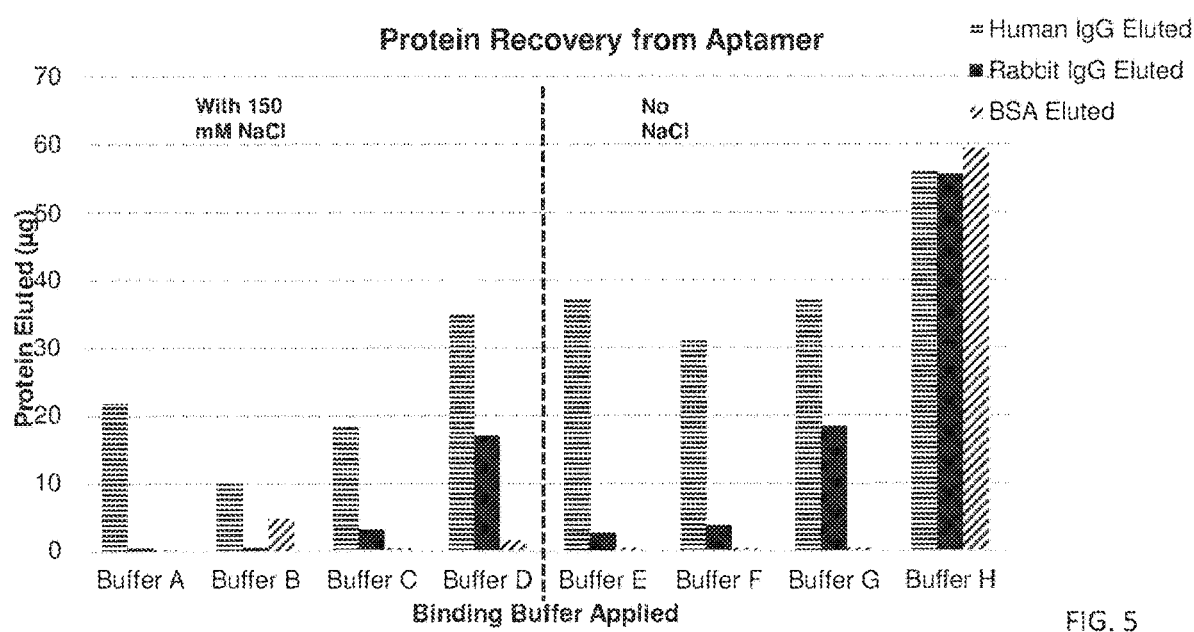
FIG. 5 is a chart showing a non-specific binding study with different binding buffers, according to an illustrative embodiment of the technology.

The binding characteristics of the aptamer are highly dependent on the composition of the buffer systems with which it is employed (See FIGS. 2A-5). Based on investigative work, it has been found that the aptamer functions with a metal-dependent mechanism. In using the aptamer, it has been observed that the presence of an appropriately selected divalent ion is essential for maintaining high affinity and selectivity (FIGS. 2A and 2B, FIG. 5). Nakamura and co-workers made the proposal that calcium ions are the most critical component to forming the affinity competent motif of this aptamer. Herein, it is shown that magnesium ions are more effective in increasing the binding capacity of the aptamer without introducing any significant amount of non-specific binding with other untargeted proteins. The concentration of magnesium cation can be between 50 µM to about 1 mM.

As used herein, the term "about" means that the numerical value is approximate and small variations would not significantly affect the practice of the disclosed embodiments. Where a numerical limitation is used, unless indicated otherwise by context, "about" means the numerical value can vary by ±10% and remain within the scope of the disclosed embodiments Meanwhile, monovalent ions have been found to serve as a disruptor to the affinity binding motif, serving as potential alternative eluents to the chelator proposed by Nakamura and co-workers. Accordingly, in some embodiments of this technology, a monovalent cation solution, including but not limited to solutions of ammonium, sodium and potassium, can be used in the form of an elution buffer to aid the recovery of target protein/analyte at neutral pH (FIGS. 3A, 3B, 4A, 4B, and 6). Moreover, in contrast to the phosphate buffers proposed by Nakamura and co-workers, it has been found that the aptamers of this invention work more advantageously in Tris buffer. In fact, a Tris buffer was found to yield better binding capacity versus a phosphate buffer when used with the same ion additives. Triethylamine (TEA), MES (2-ethanesulfonic acid), and HEPES (4-(2-hydroxyethyl)-1-piperazineethanesulfonic acid) can confer comparable advantages over a phosphate buffer.

In some embodiments, the binding buffer has a concentration of monovalent cations less than about 50 mM. The binding buffer can have a concentration of monovalent cations less than about 30 mM. In some embodiments, the pH of the binding buffer is between about 5 and about 9. The pH of the binding buffer can be between about 6 to about 8. The pH of the binding buffer can be about 7.2. For example, the pH of the binding buffer can be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. These pH values can be used to form a range, for example, from about 7.0 to about 7.4 or from about 7.1, to about 7.3.

The biofluid sample can be diluted. For example, the biofluid sample can be diluted by a factor of 2, 10, or 20. In some embodiments, the biofluid sample is diluted by a factor of 1, 3, 4, 5, 6, 7, 8, 9, 10, 11, 12, 13, 14, 15, 16, 17, 18, 19, or 20. The dilution factors can be used to form a range, for example, from about 2 to about 20 or from about 2 to about 10, or from about 10 to about 20. In some embodiments, the biofluid sample is diluted to obtain a total monovalent cation concentration of the biofluid sample of no greater than 100 mM, no greater than 50 mM or no greater than 30 mM. The total monovalent cation concentration of the diluted biofluid sample can be no greater than 100 mM, 90 mM, 80 mM, 70 mM, 60 mM, 50 mM, 40 mM, 30 mM, 20 mM, or 10 mM.

Referring to FIG. 1, the method 100 can also include eluting the adsorbed himan immunoglobulin Fc domain from the immobilized aptamer using an eluent 120. The eluent has an ammonium concentration between about 10 mM to about 1000 mM. The ammonium is in the form of tetramethylammonium, triethylammonium, ammonium formate, or ammonium acetate. The ammonium concentration can be, for example, between about 50 mM to about 500 mM. The pH of the eluent can be between about 6.5 to about 8.0.

The method 100 can also include washing the adsorbed human immunoglobulin Fc domains with the binding buffer 125. In some embodiments, the washing is done with a buffer comprising Cat The method 100 can also include analyzing the eluted human immunoglobulin Fc domain 130 with a detector. The detector can be a sandwiched enzyme linked immunosorbent assay or a mass spectrometer.

In some embodiments, the human immunoglobulin Fc domains are contained within a humanized monoclonal antibody and the method also includes purifying the humanized monoclonal antibody (not shown).

The technology also relates to a method of eluting a human immunoglobulin Fc domain from an immobilized aptamer. The method includes providing an affinity capture device having a surface having an aptamer that is at least 80% identical to SEQ ID NO 1 immobilized onto the surface of the affinity capture device. The immobilized aptamer has an adsorbed human immunoglobulin Fc domain. The adsorbed human immunoglobulin Fc domain is eluted from the immobilized aptamer using an eluent having an ammonium concentration between about 10 mM to about 1000 mM. The ammonium is in the form of tetramethylammonium, triethylammonium, ammonium formate, or ammonium acetate. The method can include any of the embodiments described herein.

The technology also relates to kits. The kits can include an affinity capture device comprising a surface having an aptamer that is at least 80% identical to SEQ ID NO 1 immobilized onto the surface of the affinity capture device. The kit can also include a vial of a binding buffer including (A) tris(hydroxymethyl)aminomethane (Tris), trimethylamine (TES), 2-ethanesulfonic acid (MES), or 4-(2-hydroxyethyl)-1-piperazineethanesulfonic acid (HEPES); (B) a magnesium cation at a concentration between about 10 µM to about 20 mM; and (C) a total monovalent cation concentration from 0 to no greater than 100 mM. The kit can include any of the embodiments described herein. This kit can also include a vial of eluent having an ammonium concentration between about 10 mM to about 1000 mM. The ammonium can be in the form of tetramethylammonium, triethylammonium, ammonium formate, or ammonium acetate. The kit can also include a vial of buffer comprising $Ca^+$. The buffer provided in the kit can be concentrated and the kit can include instructions for diluting the concentrated buffer to a working concentration. The buffer can be diluted using water. The kit can also contain instructions for performing any one of the methods described herein.

The technology relates to a kit that includes an affinity capture device comprising a surface having an aptamer that is at least 80% identical to SEQ ID NO 1 immobilized onto the surface of the affinity capture device and a vial of an eluent. The eluent has an ammonium concentration between about 10 mM to about 1000 mM. The ammonium can be in the form of tetramethylammonium, triethylammonium, ammonium formate, or ammonium acetate. The kit can include any of the embodiments described herein. The kit can include instructions for performing any of the methods described herein.

As reduced to practice, an anti-human Fc aptamer can be used with carefully defined protocol steps, namely binding, wash and elution steps. Specifically, for the binding step, the aptamer can be used with a Tris, TEA, MES or HEPES binding buffer comprised of Mg at a concentration ranging from 10 µM to 20 mM or more ideally from 50 µM to 1 mM. The concentration of monovalent cation is purposely kept minimal in this binding buffer to a concentration of less than 50 mM, more ideally less than 30 mM. In addition, the pH of the solution is designed to be between 5 and 9, more ideally 6 to 8. With this formulation and method, the binding capacity of the aptamer is improved without loss of selectivity (See FIGS. 5 and 6). This stands in contrast to the example presented by Nakamura and co-worker, wherein a buffer of 145 mM NaCl, 5.4 mM KCl, 1.8 mM $CaCl_2$. 0.8 mM $MgCl_2$, 20 mM Tris, pH 7.6 was described. Because it is critical to minimize the presence of any monovalent ions during the binding step of the aptamer capture protocol, certain embodiments of this invention entail a 2 to 20-fold dilution of sample. In this way, a complex matrix (e.g. biofluids) is reduced in its monovalent cation concentration and the negative impact of endogenous monovalent ions is minimized (FIGS. 8A-9C).

Figure 9A:
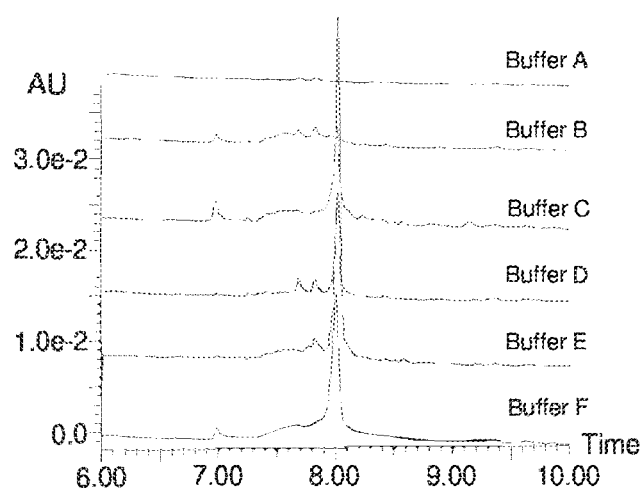
Figure 9B:
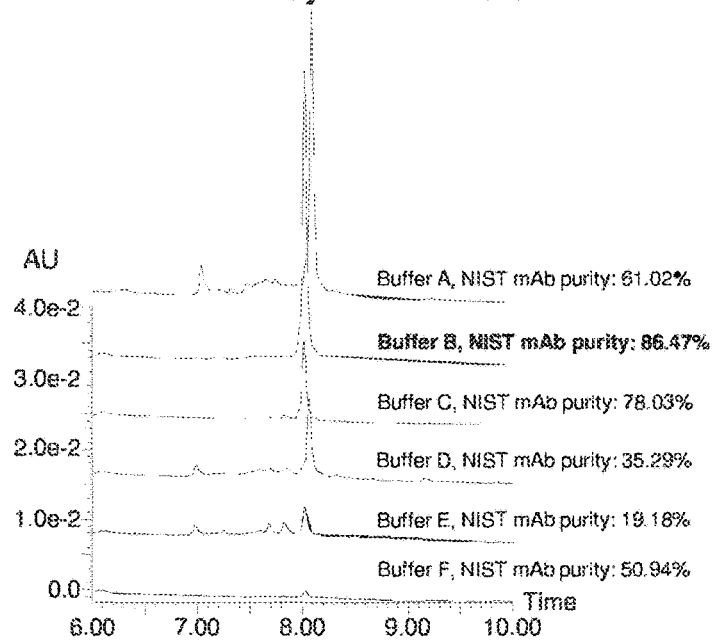

In exemplary embodiments, the method includes a wash step comprised of two procedures. The first wash procedure is performed exclusively with washing the adsorbed analyte and resin with the binding buffer. The second wash procedure preferentially performed with a Ca' containing buffer, since it has been observed to significantly decrease the non-specific binding of the aptamer ligand in complex sample matrix and to improve the purity of the captured/enriched hIgG (FIGS. 9A-9C).

In the final step of this method, the captured Fc domain can optionally be eluted by using neutral pH buffers (pH between 6.5-8.0) with chelating agents, including those described by Nakamura and co-workers, like 10 to 200 mM EDTA, malate, citrate and porphine, or with concentrated monovalent cation like $K^+$, $Na^+$, $Ag^+$, and $Cs^+$. Alternatively, the Fc domain containing analyte can be eluted with a novel buffer system, as disclosed herein, that are based on a bisphosphonate, including but not limited to medronic and etidronic, or with an MS-compatible, volatile monovalent cation, such as ammonium, tetramethylammonium or triethylammonium. In one embodiment, an elution buffer composed of 10 mM to 1000 mM, or more ideally 50 to 500 mM, ammonium formate or ammonium acetate is employed. With this type of eluent, it is possible to perform online immunoaffinity MS assays. As well, common protein A elution buffers with acidic pH (pH≤4.0), like 0.1M glycine HCl, 0.1M citric acid, 5% acetic acid or formic acid, make for another option for eluting the capture Fc domain analyte. These selections of elution condition extend the compatibility of aptamer affinity capture with many downstream processes. In some embodiments, the anti-human Fc aptamer and corresponding devices are employed to perform sample preparation for a subsequent LC or LCMS based assay, like reversed phase chromatography, ion exchange, hydrophilic interaction liquid chromatography, hydrophobic interaction chromatography, protein An affinity chromatography, subunit analysis, peptide mapping, glycan profiling and intact mass analysis. Analyses facilitated by this technology can also include online immunoaffinity capture, capillary electrophoresis, and mass spectrometry. Additionally, the methods described herein can be applied to enzyme linked immunosorbent assays (Example 7). In another embodiment, a heat-induced denaturation of the aptamer can be applied to elute captured human Fc analyte without introducing any elution buffer.

Figure 7:
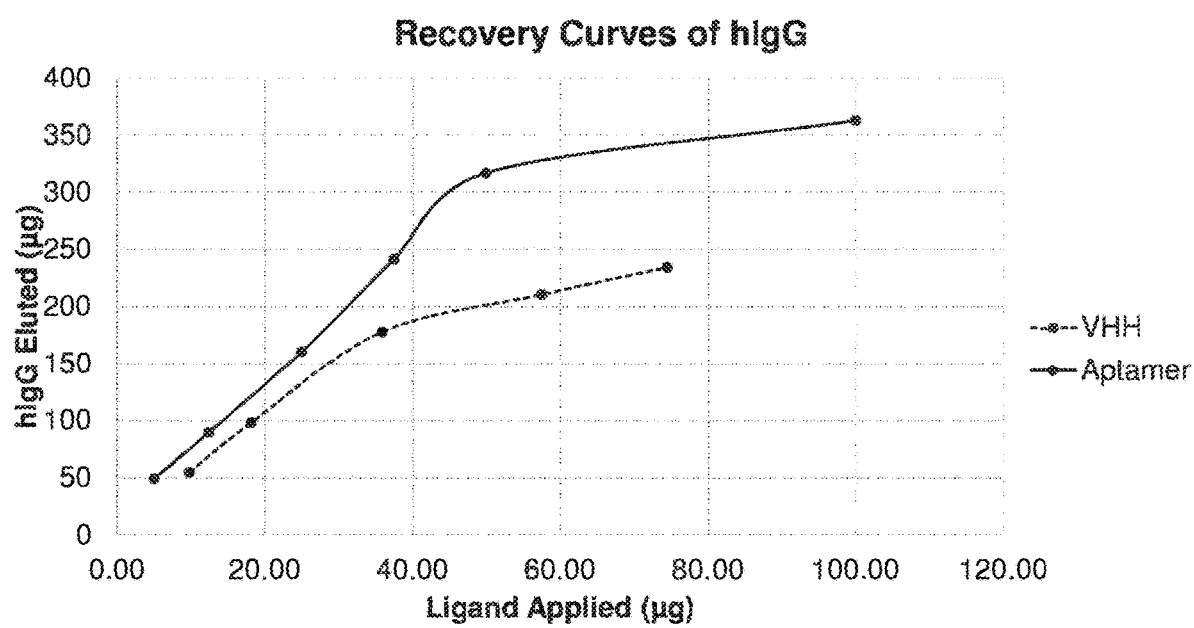
FIG. 7 is graph showing the binding capacity of aptamer versus single domain antibody $V_{HH}$, according to an illustrative embodiment of the technology.

In summary, this technology prescribes a novel sample preparation method for the selective capture of human Fc domains. Being that it is based on the use of a small affinity ligand, it shows advantageous binding capacity versus methods dependent on a full-size IgG antibody ligand and clear improvements over the prior art established by Nakamura and co-workers. (FIG. 7).

Example 1: Capture of hIgG Using Different Binding Buffers

An aptamer, having SEQ ID NO 1, was adapted from U.S. Pat. No. 8,637,656 B2 and made to contain a biotin tag at its 5'-terminus. Synthesis of the aptamer was performed by Integrated DNA Technologies (Coralville, Iowa). Each 5 µg of biotinylated aptamer was immobilized to 40 µL of high capacity streptavidin resin (commercially available from Thermo Fisher Scientific, San Jose, Calif.) in a 96-well filter plate (commercially available from MilliporeSigma, Burlington, Mass.) via a 30 minute incubation at room temperature. A positive pressure manifold (commercially available from Waters Technologies Corporation, Milford, Mass.) was utilized to drive flow through the filter plate. The amount of aptamer immobilized was determined by abosorbance at 260 nm using a DS-11 spectrophotometer (commercially available from DeNovix Inc., Wilmington, Del.). This non-covalently immobilized aptamer affinity resin was used to perform the affinity capture of 100 µg human IgG (IgG from human serum, commercially available from Sigma-Aldrich (now MilliporeSigma), St. Louis, Mo.) contained within 200 µL of several different binding buffers (specified below). After 1 hour of mixing, the resin was washed with two repeated 200 µL volumes to remove any unbound protein. Combined hIgG flow-through and washing fractions were saved to determine the amount of hIgG breakthrough. Captured human IgG was eluted with two repeat 200 µL volumes of elution buffer (200 mM EDTA, 10 mM tris, pH 7.2). The eluate was saved for hIgG recovery measurements using a fluorescence plate reader (Ex. 280 nm, Em. 370 nm; Gemini™ XPS plate reader, commercially available from Molecular Devices, San Jose, Calif.).

Figure 2B:
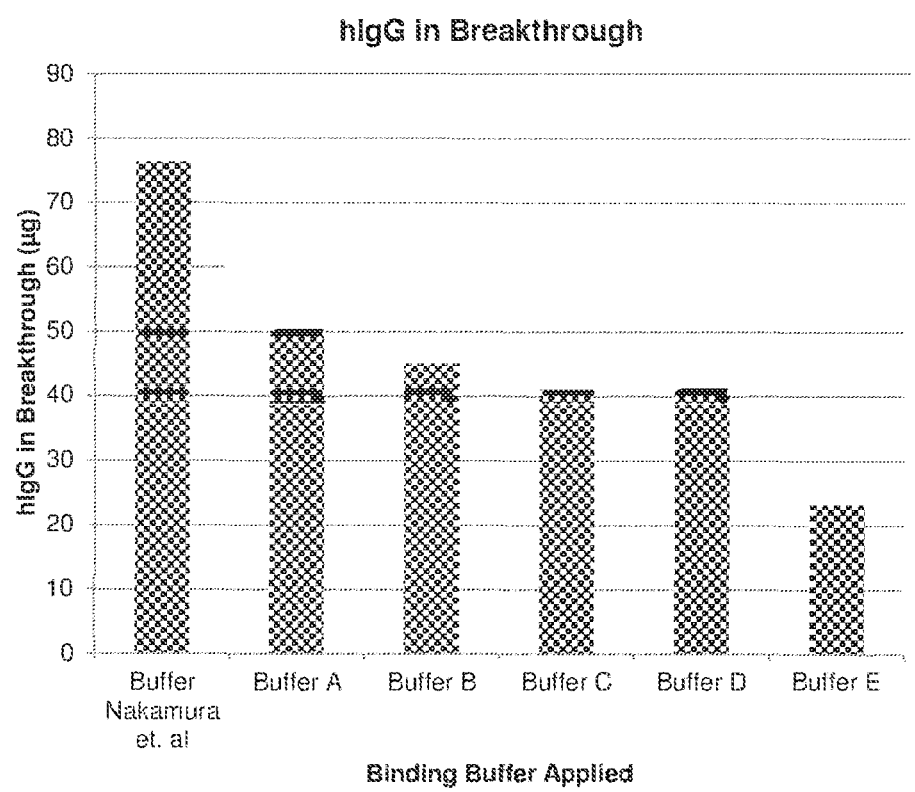
FIG. 2B is a chart showing the impact of divalent cations on hIgG in breakthrough for various binding buffers, according to an illustrative embodiment of the technology.
Figure 3A:
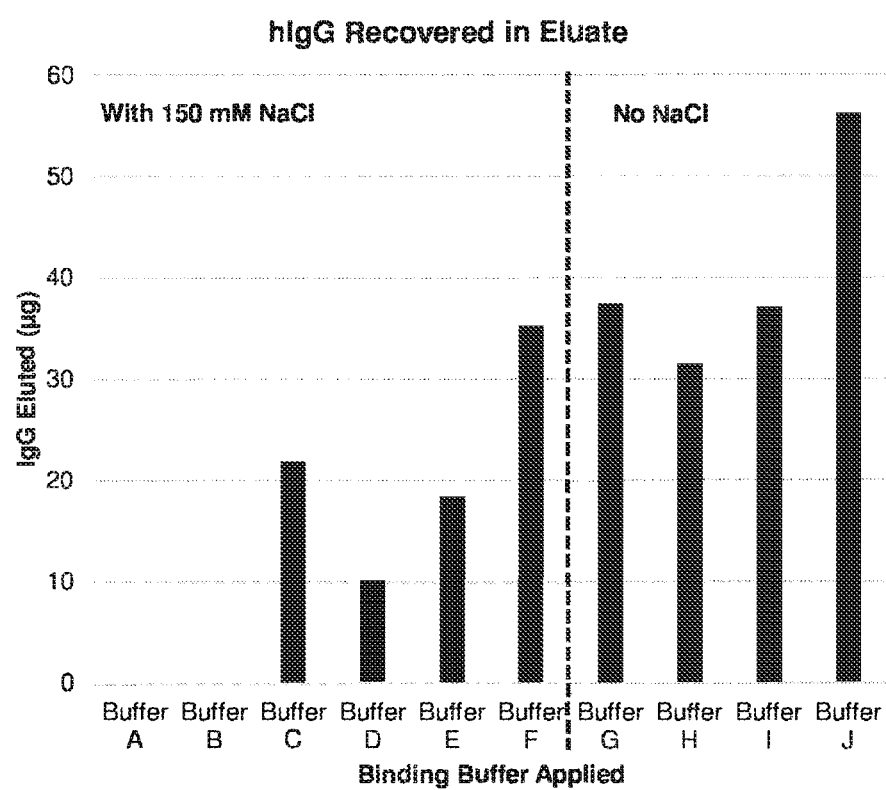
FIG. 3A is a chart showing the impact of monovalent cations on hIgG recovered in eluate for various binding buffers, according to an illustrative embodiment of the technology.
Figure 3B:
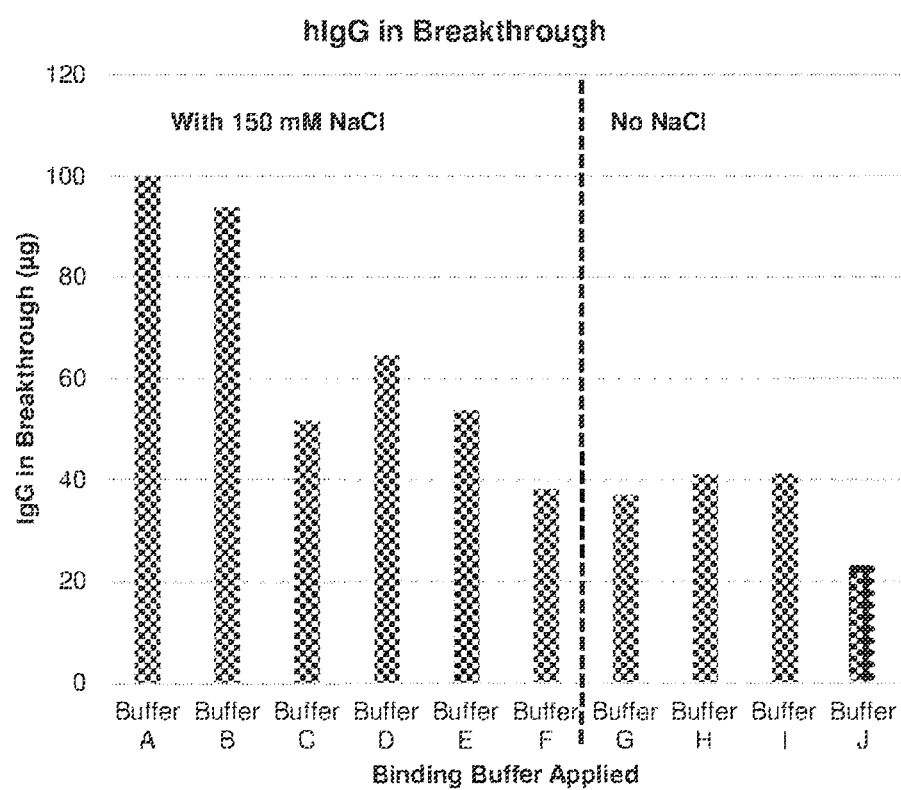
FIG. 3B is a chart showing the impact of monovalent cations on hIgG in breakthrough for various binding buffers, according to an illustrative embodiment of the technology.

The binding capacity of the aptamers, incorporated herein by reference, are highly dependent on the composition of binding buffer. To investigate the impact of divalent ions on aptamer binding characteristics, a series of Tris buffers containing different divalent cations were screened. The binding buffers tested were: 10 mM Tris buffer with 5 mM $MgCl_2$, pH 7.2; 10 mM Tris buffer with 5 mM $CaCl_2$, pH 7.2; 10 mM Tris buffer with 5 mM $MnCl_2$, pH 7.2, and 10 mM Tris buffer with 5 mM Zn acetate, pH 7.2. Tris buffer with no added cations (10 mM Tris/Tris HCl, pH 7.2) was used as a control and compared against the buffer system proposed by Nakamura and co-workers (145 mM NaCl, 5.4 mM KCl, 1.8 mM $CaCl_2$. 0.8 mM $MgCl_2$, 20 mM Tris, pH 7.6). As can be seen in FIGS. 2A and 2B, the presence of divalent cations, especially Zn' and Mg', leads to significantly improved capture and recovery of hIgG. Those two buffers stand out as exemplary embodiments for both their recovery and selectivity. On the other hand, it was surprising to notice that only 20% of loaded hIgG was captured when the buffer proposed by Nakamura and co-workers was employed (comparative example), which means the presence of concentrated sodium chloride (NaCl) and the combination of multiple divalent/monovalent cations in buffer inhibit the binding capacity of aptamer.

That there is such a negative impact on hIgG capture from the presence of monovalent cations was again demonstrated by comparing binding capacity and protein recovery using binding buffers both containing and not containing $Na^+$ or $K^+$ cations. The binding buffers explored in this particular study included a) buffers without 150 mM NaCl: 10 mM Tris buffer with 5 mM $MgCl_2$, pH 7.2; 10 mM Tris buffer with 5 mM $CaCl_2$, pH 7.2; 10 mM Tris buffer with 5 mM $MnCl_2$, pH 7.2, and 10 mM Tris buffer with 5 mM Zn acetate, pH 7.2 versus b) matching buffers made to also contain 150 mM NaCl as well as 10 mM Tris buffer with 5 mM KCl, 150 mM NaCl, pH 7.2. Tris buffer containing 150 mM NaCl was also used as a control. The results of this study are summarized in FIGS. 3A and 3B. From these data, it appears that the presence of 150 mM NaCl in a divalent cation containing binding buffer is disruptive to the adsorption of hIgG onto the immobilized aptamer, as is manifest in a significant decrease in aptamer binding capacity and hIgG recovery. Adding potassium cations (K) into the sodium chloride (NaCl) containing binding buffer had no effect toward improving recovery. This result is consistent with the observed binding characteristics of the aptamer when using the binding buffer proposed by Nakamura and co-workers, being that it contains relatively high concentrations of monovalent cations—that is, monovalent cations at concentrations greater than 10 mM.

The type of aptamer binding buffer is yet another factor that affects capture efficiency. Phosphate-based buffers were used here as alternatives for the binding step. Three phosphate buffers were applied in this study including: 20 mM $Na_2HPO_3$ with no added NaCl, pH 7.0; 20 mM $Na_2HPO_3$ with 150 mM NaCl, pH 7.0; and 20 mM $Na_2HPO_3$ with 5 mM $MgCl_2$, pH 7.0. 10 mM Tris buffer with the same ionic components were employed as a control. As shown in FIGS. 4A and 4B, Tris buffer provided better binding capacity than phosphate buffer when used with the same ion additives. When the aptamer was used with phosphate-only buffer, it showed almost no affinity for IgG, while its affinity could be partially recovered via the addition of 5 mM $Mg^{2+}$. According to the reported crystal structure of the hIgG-aptamer complex pertinent to this technology, it is reasonable to suggest that phosphate might interrupt the folding of the aptamer into its active affinity motif.

In summary, 10 mM Tris buffer containing divalent cations like $Zn^{2+}$ or $Mg^{2+}$ stand out as exemplary embodiments of this technology. Additional experiments have been performed to demonstrate the usability of these buffers and their results are detailed below.

Example 2: Impact of Binding and Elution Buffer on Aptamer Selective Capture

The presence of divalent cations in the binding buffer has the potential to facilitate the activation of the aptamer affinity motif, yet it could also instigate non-specific binding. Accordingly, we also aimed to address the non-specific binding of the aptamer. The biotinylated aptamer was immobilized as described in Example 1 and subsequently used for hIgG capture. Different divalent cation containing Tris binding buffers (Mg, Ca, Mn, Zn) were prepared with and without 150 mM NaCl and thereafter employed in this study. The compositions of these binding and elution buffers were listed earlier in Example 1. Rabbit IgG (rIgG) (commercial available from Sigma-Aldrich (now MilliporeSigma), St. Louis, Mo.) and bovine serum albumin (BSA) (commercial available from Sigma-Aldrich (now MilliporeSigma), St. Louis, Mo.) were used as two negative controls to investigate the non-specific binding of the aptamer. 100 µg of hIgG, rIgG and BSA were loaded to the non-covalently immobilized aptamer resin using 200 µL volumes of the various binding buffers. After binding and washing steps, captured proteins were eluted with elution buffer and protein recovery in each eluate was measured using a fluorescence plate reader.

The results on protein recovery are summarized in FIG. 5. Interestingly, buffer containing Zn' brought about a high level of non-specific binding with all proteins tested, especially when no NaCl was present. Therefore, Zn containing binding buffer was deemed to be unsuitable for this method. The same issue was observed with $Mn^{2+}$ containing buffer, which also produced a high level of non-specific binding with rIgG. In light of these results, it should be noted that some NaCl can be included in a wash buffer so as to attenuate some types of non-specific binding.

Further analysis of the results shows that a buffer comprised of $Mg^{2+}$ is the most promising for binding, as it provided effective capture with negligible non-specific binding. Nevertheless, it can be shown that having different concentrations of $Mg^{2+}$ in the binding buffer can be of impact to binding capacity. As summarized in FIG. 6, a binding buffer with $Mg^{2+}$ concentration between 50 μM to 1 mM resulted in the highest hIgG capture and recovery among all conditions tested. It seems, therefore, that the use of a binding buffer with more than 20 mM or less than 10 μM $Mg^{2+}$ might result in sub-optimal hIgG binding.

Figure 6:
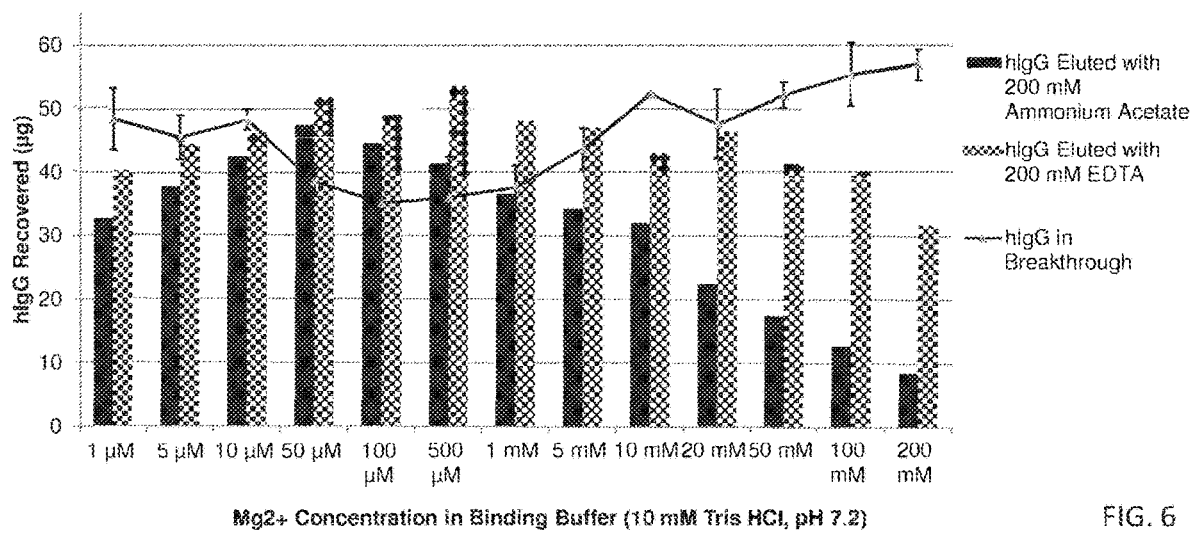
FIG. 6 is a chart showing the impact of magnesium concentration in binding buffer and section of elution buffer, according to an illustrative embodiment of the technology.

In another investigation, we chose to investigate the use of concentrated ammonium acetate buffer for hIgG elution (FIG. 6). Since our preliminary results indicated that binding is highly dependent on the presence of certain divalent cations, we aimed to see if a competing cation can be used to displace the divalent cation from the hIgG-aptamer complex and thereby elute the captured hIgG. As proposed by Nakamura, an EDTA buffer can be used as an elution buffer. However, this non-volatile chelating agent can cause problems for downstream mass spectrometric (MS) analysis. In contrast, a buffer with a competing volatile monovalent cation like ammonium acetate ($NH_4OAc$), ammonium formate or ammonium bicarbonate can be a more MS friendly elution buffer. To this point, 200 mM ammonium acetate, pH 7.2 was used to elute captured hIgG from the aptamer and the quality of the eluate was compared to that obtained with 200 mM EDTA elution buffer. As shown in FIG. 6, the elution efficiency of concentrated $NH_4OAc$ was highly dependent on $Mg^{2+}$ concentration in the binding buffer. For binding buffers comprised of 50 μM to 10 mM Mg', the recovery of hIgG with $NH_4OAc$ can be 80-90% of that obtained using an EDTA elution buffer.

In summary, 10 mM Tris binding buffer with $Mg^{2+}$ can minimize undesirable non-specific binding and provide exemplary binding capacity. The ideal $Mg^{2+}$ concentration in the binding buffer is between 10 μM and 10 mM, more ideally 50 μM to 1 mM. Importantly, with this selected binding buffer, concentrated ammonium buffer (e.g. 200 mM ammonium acetate) can be used to achieve comparatively high recovery with an MS-friendly elution buffer.

Example 3: Evaluation of Aptamer Binding Capacity

To determine the binding capacity of the aptamer, protocols established with this technology were employed to sample preparations involving amounts of hIgG exceeding 500 μg. 5 μg, 12.5 μg, 25 μg, 37.5 μg, 50 μg and 100 μg of biotinylated aptamer were immobilized onto 40 μL of streptavidin resin. Procedures for aptamer immobilization and hIgG capture were identical to those described in previous examples. The recovery of hIgG was plotted against the amount of aptamer immobilized to estimate the maximum binding capacity of the aptamer (FIG. 7). 10 mM Tris, 0.5 mM Mg, pH 7.2 and 200 mM EDTA, 10 mM Tris, pH 7.2 were employed for binding and elution, respectively. According to the hIgG recovery curve, it can be seen that by using the optimized buffers and protocols of this technology, the maximum binding capacity of aptamer is close to 6.5 μg hIgG/μg immobilized aptamer, which is about 20 times higher than that estimated to be possible with a full-length IgG-based anti-human Fc antibody. It is also worth mentioning that the surface coverage of the aptamer was constrained in this testing by the limitations of noncovalent immobilization to a streptavidin resin. A higher binding capacity can be predicted for an aptamer prepared by way of direct immobilization. The coverage of the immobilized aptamer can be about 1 to about 1000 nmol/m². To minimize costs, lower coverage immobilization might be preferred. Yet, to achieve high binding capacity surfaces, higher coverages are desirable.

In yet another example, the capabilities of this aptamer-based affinity capture has been compared to a commercialized nanobody ligand for human Fc capture. A nanobody derived from a camelid $V_HH$ domain was previously developed and is now commercially available in the form of Thermo-Fisher Scientific CaptureSelect® branded technology. In this study, anti-human Fc $V_HH$ ligand was recombinantly expressed (GenScript, Piscataway, N.J.) from a sequence adapted from U.S. Pat. No. 9,040,666 B2 (incorporated by reference herein in its entirety) and designed to have a C-terminal extension consisting of an extra cysteine residue, TEV protease cleavage site and His-tag. The obtained nanobody was treated with ProTEV (commercially available from Promega, Madison, Wis.) to remove its His-Tag and thereafter derivatized with EZ-Link™, idoacetyl-PEG2 Biotin (commercially available from Thermo-Fisher Scientific, San Jose, Calif.). The purity of the resulting biotinylated $V_HH$ was assessed by LCMS and determined to be greater than 80% biotinylated. Biotinylated $V_HH$ was non-covalently immobilized to 40 μL of streptavidin resin slurry and used to capture hIgG using the same procedure as the aptamer. The amount of $V_HH$ immobilized was measured by absorbance at 280 nm using a DS-11 spectrophotometer (commercially available from DeNovix Inc., Wilmington, Del.). 20 mM phosphate, pH 7.0 and 0.1 M glycine-HCl, pH 2.7 was recommended by CaptureSelect literature from Thermo Fisher Scientific as being appropriate binding and elution buffers. As shown in FIG. 7, the maximum binding capacity of this $V_HH$ based ligand (5 μg hIgG/μg immobilized $V_HH$) was lower than that of the aptamer.

Example 4: Capture of hIgG from Biofluid

Figure 8A:
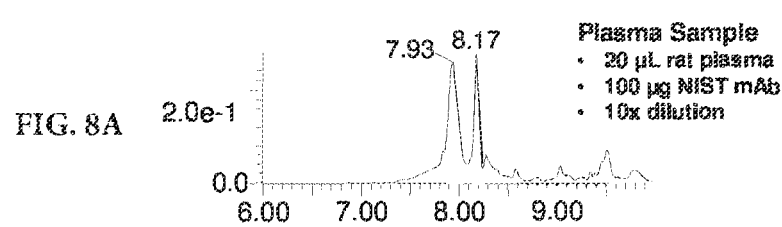
FIGS. 8A-8C depict an example of non-specific binding of aptamer against endogenous protein from biofluids.
Figure 8B:
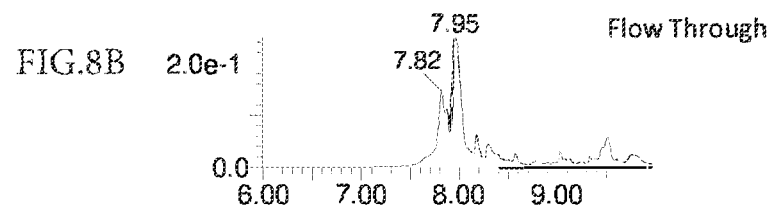
Figure 8C:
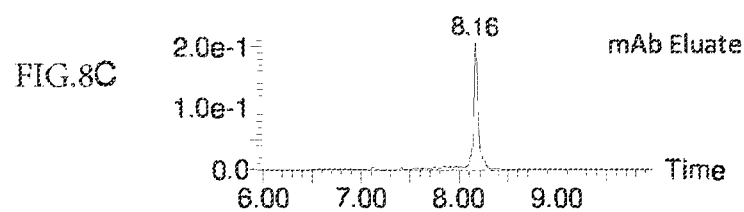
Figures 8D, 8E:
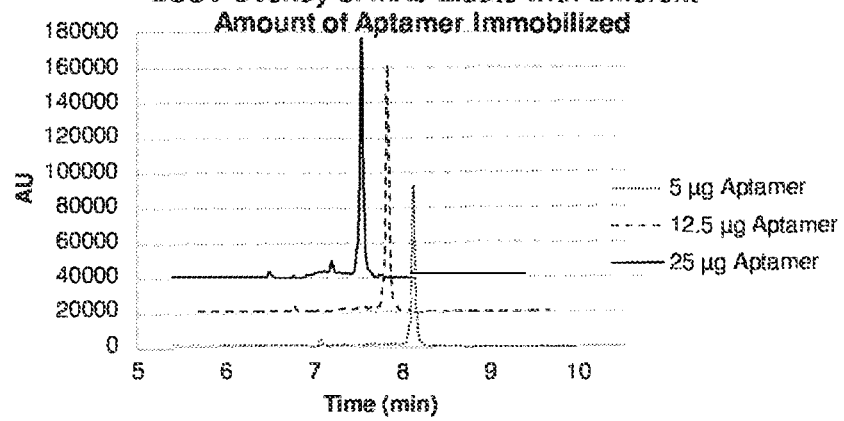
FIGS. 8D-8E depict an example of non-specific binding of aptamer against endogenous protein from biofluids. LC-UV profile of eluate fractions recovered from 40 µL of streptavidin resin with 5 µg, 12.5 µg and 25 µg aptamer immobilized. The loading and recovery of NIST mAb and plasma protein were calculated accordingly and summarized in table (8E). Experimental details can be found in Example 4.

To investigate the selectivity of purifying human Fc domains from biofluid matrices, different amounts of NIST mAb (NIST Reference Material 8671) were spiked into rat plasma, followed by affinity capture with non-covalently immobilized aptamer using the protocols described by this invention. The purity of flow-through, washing and eluate fractions was analyzed using an ACQUITY® UPLC® H-Class Bio (commercially available from Waters Technologies Corporation, Milford, Mass.) with an ACQUITY® BEH300 C4 column (1.7 μm, 2.1×100 nm) (commercially available from Waters Technologies Corporation, Milford, Mass.). The protein concentration of each fraction was determined using a fluorescence plate reader (Gemini XPS, (commercially available from Molecular Devices, LLC, San Jose, Calif.); Ex. 280 nm, Em. 370 nm) and re-calculated according to the chromatographic purity assessment. FIG. 8A-C shows example data from the purification of 100 µg of NIST mAb from 20 µL rat plasma matrix using 12.5 µg of immobilized aptamer. After purification, about 85% of the spiked NIST mAb was recovered with purity increasing from 10.6% to 72.4%.

The small portion of impurity in the purified NIST mAb eluate was determined to be the non-specific binding of rat plasma endogenous proteins to the aptamer. The competition in binding between NIST mAb and plasma protein was investigated by loading 20 µL of rat plasma containing 50 µg of NIST mAb onto an increasing amount of immobilized aptamer (5 µg, 12.5 µg, 25 µg). The result of this experiment is summarized in FIG. 8D-E. From which, it is possible to observe that the binding ratio of NIST mAb to plasma protein is close to 7:3 (from UV measurement) for the current experimental approach. These data suggest that non-specific binding can be further reduced.

Hence, an extra washing step (second washing) was applied before the elution step. To test out this optional protocol step, 20 µL of plasma and 25 µg of NIST mAb were diluted with binding buffer to 200 µL then loaded onto 40 µL of streptavidin resin wherein 5 µg of aptamer was non-covalently immobilized. After the first washing with binding buffer, two 200 µL volumes of each potential second wash-buffers was applied, including the binding binding buffer proposed by Nakamura and co-workers (10 mM Tris, 5 mM $CaCl_2$, pH 7.2); 20 mM phosphate, pH 7.0; 0.1 M glycine-HCl, pH 2.7; 150 mM NaCl and binding buffer (control). Elution was thereafter performed with an EDTA buffer. Herein, the second washing and elution fractions were collected and analyzed by LC-UV analysis. As shown in FIG. 9A, neither the binding buffer proposed by Nakamura et al nor 20 mM phosphate, 0.1 M glycine and 150 mM NaCl were found to be suitable secondary washing buffers. In both cases, the captured NIST mAb was eluted together with plasma impurities. On the other hand, a Tris buffer containing 5 mM $CaCl_2$) was able to selectively wash off impurities from the aptamer. According to FIGS. 9B and 9C, the immobilized aptamer showed the best NIST mAb recovery, together with the highest purity, after the application of a secondary washing step based on 5 mM $CaCl_2$) containing tris buffer. Therefore, this Ca' containing buffer is a recommended, yet optional, secondary washing buffer for use in an optimized protocol for capturing human Fc domains from biofluid samples. An exemplary embodiment of this invention is outlined in following protocol.

Example 5: Exemplary Protocol for the Capture of a Humanized mAb Based Therapeutic Protein from a Preclinical Type Biofluid Sample This exemplary protocol is intended for use with an immobilized aptamer material or device.
Buffers Used:
Binding/$1^{st}$ washing buffer: 10 mM Tris, 0.5 mM $MgCl_2$, pH 7.2
$2^{nd}$ (secondary) washing buffer: 10 mM Tris, 5 mM $CaCl_2$, pH 7.2
Elution buffer: 10 mM Tris, 200 mM EDTA, pH 7.2, or 200 mM Ammonium acetate, pH 7.2 (for MS analysis)
Biofluid Sample Preparation:
It is recommended to dilute a biofluid sample at least ten-fold with binding buffer before loading sample onto the immobilized aptamer. For example, dilute 10 µL of biofluid sample with 90 µL binding buffer to make a final volume of 100 µL.

Binding Step:
Equilibrate the immobilized aptamer resin/device with binding buffer (~10 column volumes (CV) versus the volume of affinity resin/bed)
Load diluted biofluid sample onto the immobilized aptamer
Incubate device at room temperature for 1 hour with mixing. (e.g. plate shaker at 5-600 rpm)
Remove flow-through solution from resin/device
Washing Step:
Perform the $1^{st}$ washing step using binding buffer (~10 CV of resin used)
Remove $1^{st}$ washing solution from the resin/device
Perform the $2^{nd}$ washing step using the secondary washing buffer (~10 CV of resin used).
Remove the secondary wash solution from the resin/device
Elution Step:
Elute captured human Fc analyte with desired elution buffer (~10 CV of resin can be used, though the volume of elution buffer can be varied as needed)
Save fractions as eluate for downstream analysis Example 6: Online Immunoaffinity Capture MS Analysis Example Immobilized anti-human Fc aptamer can be employed for online immunoaffinity capture MS to facilitate the identification and quantitation of humanized biotherapeutics. In some embodiments, an immunoaffinity column is packed with immobilized aptamer resin and coupled directly with LCMS for analysis. A solvent manager can be used in this application to deliver binding buffer, the secondary washing buffer and MS compatible elution buffer. Elution buffer described here includes but is not limited to volatile monovalent salts like ammonium formate, ammonium acetate, ammonium bicarbonate, tetramethylammonium or triethylammonium; volatile acids like formic acid, acetic acid, TFA or DFA; volatile solvents like acetonitrile and methanol. To avoid contamination of MS, LC flow-through can be diverted to waste for binding and washing steps and then switched back to MS for the elution step. Depending on LC settings, the first 30 seconds to 2 minutes of effluent from the immunoaffinity column can also be directed to waste. Alternatively, an MS-compatible washing buffer can be employed. Upon elution and detection by MS, retention time, peak area and m/z values are used together to characterize components of the sample. In another embodiment, the packed aptamer immunoaffinity column can be applied to a two-dimensional (2D) LCMS system for more comprehensive analyses. A secondary analytical column involved in such a 2D-LCMS system can be equipped with a multitude of techniques, including but not limited to, normal phase separation, reverse phase separation, size-exclusive separation, ion-exchange separation, HILIC separation, HIC separation, affinity capture or enzymatic digestion.

Example 7: Anti-Human Fe ELISA Example

Being an anti-human Fc affinity ligand, the aptamer sequences incorporated herein by reference can be used along with aspects of this invention to establish a sensitive enzyme linked immunosorbent assay (ELISA) for accurate quantification of human IgG or humanized therapeutics with Fc domain. In some embodiments, anti-human Fc aptamer is coated onto the surface of an ELISA plate and used to capture target IgG from biofluids. The selected binding buffer described above is applied to ensure that a desired binding capacity and specificity are achieved. Unbound impurities are then washed from the plate using one or more of the described washing buffers. In a typical embodiment, a secondary detection ligand with enzyme label, such as horse radish peroxidase, is utilized to create a sandwich immunoassay. This detection ligand binds to human IgG at one or more domain, including but not limited to CH1, light chain κ, light chain λ, VH or VL. After binding of the detection ligand, a substrate, usually TMB, is added to the ELISA plate and catalyzed by the enzyme label to produce a colored product that the concentration can be measured using a UV plate reader. In an alternative embodiment, the aptamer ligand is free in solution yet modified to contain an enzyme label. A direct ELISA measurement can then be performed with the binding protocols described by the instant technology. In yet another embodiment, the aptamer ligand is modified to contain the enzyme label itself so as to facilitate an indirect ELISA measurement.

Those skilled in the art will recognize, or be able to ascertain using no more than routine experimentation, numerous equivalents to the specific procedures described herein. Such equivalents were considered to be within the scope of this technology and are covered by the following claims. The contents or all references, issued patents, and published patent applications cited throughout this application are hereby incorporated by reference.

SEQUENCE LISTING TABLE

| SEQ ID NO: | DESCRIPTION | SEQUENCE |
|---|---|---|
| 1 | 23-nucleotide aptamer | 5' terminus G G rA rG rG [i2FU] rG C [i2FU] C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides |
| 2 | 23-nucleotide aptamer | 5' terminus-G G rA rG rG [i2FU] rG [i2FC] [i2FU] [i2FC] [i2FC] G A A A rG rG rA rA [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 3 | 23-nucleotide aptamer | 5' terminus-G G rA rG rG [i2FU] rG [i2FC] [i2FU] [i2FC] C G A A A rG rG rA rA [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 4 | 23-nucleotide aptamer | 5' terminus - G(OMe) G(OMe) rA rG rG [i2FU] rG [i2FC] [i2FU] [i2FC] [i2FC] G(OMe) A(OMe) A(OMe) A(OMe) rG rG rA rA [i2FC] [i2FU] C(OMe)C(OMe) - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe) and A(OMe) represent 2'-methoxy substituted nucleotides. |
| 5 | 23-nucleotide aptamer | 5' terminus - G G rA rG rG [i2FU] rG C U(OMe) C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe) represents 2'-methoxy substituted nucleotides. |
| 6 | 23-nucleotide aptamer | 5' terminus - G(OMe) G(OMe) rA rG rG [i2FU] rG [i2FC] U(OMe) [i2FC] [i2FC] G(OMe) A(OMe) A(OMe) A(OMe) rG rG rA rA [i2FC] [i2FU] C(OMe) C(OMe) - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe), C(OMe), G(OMe) and A(OMe) represent 2'-methoxy substituted nucleotides. |
| 7 | 23-nucleotide aptamer | 5' terminus - G(OMe) G(OMe) rA rG rG [i2FU] rG [i2FC] [i2FU] C(OMe) [i2FC] G(OMe) A(OMe) A(OMe) A(OMe) rG rG rA rA [i2FC] [i2FU] C(OMe) C(OMe) - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe)and A(OMe) represent 2'-methoxy substituted nucleotides. |

SEQUENCE LISTING TABLE

| SEQ ID NO: | DESCRIPTION | SEQUENCE |
|---|---|---|
| 8 | 23-nucleotide aptamer | 5' terminus - G(OMe) G(OMe) rA rG rG [i2FU] rG [i2FC] [i2FU] [i2FC] C(OMe) G(OMe) A(OMe) A(OMe) A(OMe) rG rG rA rA [i2FC] [i2FU] C(OMe) C(OMe) - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. C(OMe), G(OMe) and A(OMe) represent 2'-methoxy substituted nucleotides. |
| 9 | 23-nucleotide aptamer | 5' terminus - G G rA rG [i2FG] [i2FU] rG C [i2FU] C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 10 | 23-nucleotide aptamer | 5' terminus - G G rA rG rG [i2FU] [i2FG] C [i2FU] C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 11 | 23-nucleotide aptamer | 5' terminus - G G rA rG rG [i2FU] rG rC [i2FU] C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 12 | 23-nucleotide aptamer | 5' terminus - G G rA rG rG [i2FU] rG C rU C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. |
| 13 | 23-nucleotide aptamer | 5' terminus - G G rA rG rG [i2FU] rG C U(OMe) C C G A A A rG rG A A [i2FC] [i2FU] C C - 3' terminus where A, C, G, U represent four nucleobases. Uppercase letter corresponds to deoxyribonucleotide, and rX indicates ribonucleotide. [i2FC] and [i2FU] denote 2'-fluoro substituted pyrimidine nucleotides. U(OMe) represents 2'-methoxy substituted nucleotides. |

The invention claimed is:

1. A method of capturing human immunoglobulin Fc domains in a biofluid sample, the method comprising:
   providing an affinity capture device comprising a surface having an aptamer that is at least 80% identical to SEQ ID NO 1 immobilized onto the surface of the affinity capture device;
   diluting the biofluid sample with a binding buffer comprising:
   (A) tris(hydroxymethyl)aminomethane (Tris), trimethylamine (TES), 2-ethanesulfonic acid (MES), or 4-(2-hydroxyethyl)-1-piperazineethanesulfonic acid (HEPES);
   (B) a magnesium cation at a concentration between about 10 μM to about 20 mM; and
   (C) a total monovalent cation concentration from 0 to no greater than 100 mM; and
   adsorbing the human immunoglobulin Fc domains in the biofluid sample to the aptamer with the binding buffer.

2. The method of claim 1, wherein the binding buffer has a concentration of monovalent cations less than about 50 mM.

3. The method of claim 1, wherein the binding buffer has a concentration of monovalent cations less than about 30 mM.

4. The method of claim 1, wherein the pH of the binding buffer is between about 5 and about 9.

5. The method of claim 4, wherein the pH of the binding buffer is between about 6 to about 8.

6. The method claim 5, wherein the pH of the binding buffer is about 7.2.

7. The method of claim 1, further comprising eluting the adsorbed human immunoglobulin Fc domain from the immobilized aptamer using an eluent having an ammonium concentration between about 10 mM to about 1000 mM, wherein the ammonium is in the form of tetramethylammonium, triethylammonium, ammonium formate, or ammonium acetate.

8. The method of claim 1, further comprising washing the adsorbed human immunoglobulin Fc domains with a buffer comprising $Ca^+$.

9. The method of claim 1, wherein the concentration of the magnesium cation is between about 50 μM to about 1 mM.

10. A kit comprising:
    an affinity capture device comprising a surface having an aptamer that is at least 80% identical to SEQ ID NO 1 immobilized onto the surface of the affinity capture device; and
    a vial of a binding buffer comprising:
    (A) tris(hydroxymethyl)aminomethane (Tris), trimethylamine (TES), 2-ethanesulfonic acid (MES), or 4-(2-hydroxyethyl)-1-piperazineethanesulfonic acid (HEPES);
    (B) a magnesium cation at a concentration between about 10 μM to about 20 mM; and
    (C) a total monovalent cation concentration from 0 to no greater than 100 mM.

11. The kit of claim 10, wherein the binding buffer has a concentration of monovalent cations less than about 50 mM.

12. The kit of claim 10, wherein the binding buffer has a concentration of monovalent cations less than about 30 mM.

13. The kit of claim 10, wherein the pH of the binding buffer is between about 5 and about 9.

14. The kit of claim 13, wherein the pH of the binding buffer is between about 6 to about 8.

15. The kit of claim 14, wherein the pH of the binding buffer is about 7.2.

16. The kit of claim 10, wherein the concentration of the magnesium cation is between about 50 μM to about 1 mM.

17. The kit of claim 10, further comprising a vial of an eluent having an ammonium concentration between about 10 mM to about 1000 mM, wherein the ammonium is in the form of tetramethylammonium, triethylammonium, ammonium formate, or ammonium acetate.

18. The kit of claim 10, further comprising a vial of a buffer comprising $Ca^+$.

19. The kit of claim 18, wherein the buffer is concentrated and the kit further comprises instructions for diluting the concentrated buffer to a working concentration using water.

20. The kit of claim 10, further comprising instructions for performing a method of capturing human immunoglobulin Fc domains in a biofluid sample according to claim 1.

21. The method of claim 8, wherein the buffer comprising $Ca^+$ is concentrated, further comprising diluting the concentrated buffer comprising $Ca^+$ to a working concentration using water.

* * * * *

SEQUENCE LISTING

<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1
ggaggugcuc cgaaaggaac ucc    23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide -continued

<400> SEQUENCE: 2
ggaggugcuc cgaaaggaac ucc                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ggaggugcuc cgaaaggaac ucc                                              23

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gcgcaggugc uccgcacaca cggaacuccc c                                     31

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ggaggugcuc ccgaaaggaa cucc                                             24

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gcgcaggugc ucccgcacac acggaacucc cc                                    32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
gcgcaggugc ucccgcacac acggaacucc cc                                32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gcgcaggugc ucccgcacac acggaacucc cc                                32

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ggaggugcuc cgaaaggaac ucc                                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
ggaggugcuc cgaaaggaac ucc                                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ggaggugcuc cgaaaggaac ucc                                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 12
ggaggugcuc cgaaaggaac ucc                                              23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ggaggugcuc ccgaaaggaa cucc                                             24
```